(12) United States Patent
Scaria et al.

(10) Patent No.: US 10,822,391 B2
(45) Date of Patent: Nov. 3, 2020

(54) FUSION PROTEINS AND METHODS FOR INHIBITING IL-17 PATHWAYS

(75) Inventors: Abraham Scaria, Framingham, MA (US); Gary White, Marlborough, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 12/731,772

(22) Filed: Mar. 25, 2010

(65) Prior Publication Data

US 2011/0052585 A1      Mar. 3, 2011

Related U.S. Application Data

(63) Continuation of application No. PCT/US2008/011086, filed on Sep. 25, 2008.

(60) Provisional application No. 60/974,892, filed on Sep. 25, 2007.

(51) Int. Cl.
    C07K 19/00    (2006.01)
    C07K 14/715   (2006.01)
    A61K 38/00    (2006.01)

(52) U.S. Cl.
    CPC .......... *C07K 14/7155* (2013.01); *A61K 38/00* (2013.01); *C07K 2319/30* (2013.01); *C12N 2750/14143* (2013.01)

(58) Field of Classification Search
    None
    See application file for complete search history.

(56) References Cited

U.S. PATENT DOCUMENTS

| | | | |
|---|---|---|---|
| 5,869,286 A * | 2/1999 | Yao et al. | 435/69.1 |
| 6,849,719 B2 * | 2/2005 | Shi et al. | 530/388.22 |
| 7,005,412 B1 | 2/2006 | Troutt | |
| 7,094,566 B2 | 8/2006 | Medlock et al. | |
| 7,256,264 B2 | 8/2007 | Goddard et al. | |
| 7,338,930 B2 | 3/2008 | Troutt | |
| 7,928,072 B2 * | 4/2011 | Scaria et al. | 514/20.6 |
| 2011/0268735 A1 | 11/2011 | Scaria et al. | |

FOREIGN PATENT DOCUMENTS

| WO | WO 99/02711 | 1/1999 |
|---|---|---|
| WO | WO2005/123778 A | 12/2005 |
| WO | WO2006/031689 A | 3/2006 |
| WO | WO2006/068987 | 6/2006 |
| WO | WO2006/088833 A | 8/2006 |
| WO | WO2007/076524 | 7/2007 |

OTHER PUBLICATIONS

Chen et al. Fusion Protein Linkers: Effects on Production, Bioactivity, and Pharmacokinetics. Fusion Protein Technologies for Biopharmaceuticals: Applications and Challenges (book), Editor(s): Stefan R. Schmidt; Chapter 4, pp. 57-73; Feb. 12, 2013.*
International Search Report for PCT/US2008/011086 dated Jul. 4, 2009.
Li, et al., Gene transfer of soluble interleukin-17 receptor prolongs cardiac allograft survival in a rat model, European Journal of Cardio-Thoracic Surgery, vol. 29, No. 5, May 1, 2006, pp. 779-783.
Vangelista, et al., A minimal receptor-Ig chimera of human FcepsilonRI alpha-chain efficiently binds secretory and memorane IgE, Protein Eingineering, Oxford University Press, vol. 15, No. 1 Jan. 1, 2002, pp. 51-57.
Belke, et al., In vivo gene delivery of HSP70i by adenovirus and adeno-associated virus preserves contractile function in mouse heart following ischemia-reperfusion, American Jouranl of Physiology, Heart and Circulatory Physiology, vol. 291, Dec. 2006.
Yao, et al., Herpesvirus saimiri encodes a new cytokine, IL-17, which binds to a novel cytokine receptor, Immunity, vol. 3, No. 6, Dec. 1, 1995, pp. 811-821.
Gaffen, Sarah L., An overview of IL-17 function and signaling, Cytokine, vol. 43, No. 3, Sep. 2008, pp. 402-407.
International Preliminary Report on Patentability for PCT/US2008/011086, dated Mar. 30, 2010.
Antonysamy et al., "Evidence for a Role of IL-17 in Organ Allograft Rejection: IL-17 Promotes the Functional Differentiation of Dendritic Cell Progenitors", The Journal of Immunology, pp. 577-584 (1998).
Bush et al., "Reduction of Joint Inflammation and Bone Erosion in Rat Adjuvant Arthritis by Treatment With Interleukin-17 Receptor IgG1 Ff Fusion Protein", Arthritis & Rheumatism, 46(3):802-805 (2002).
Lankford et al., "A Unique Role for IL-23 in Promoting Cellular Immunity", Journal of Leukocyte Biology, 73:49-56 (2003).
Pechan et al., "Novel Anti-VEGF Chimeric Molecules Delivered by AAV Vectors for Inhibition of Retinal Neovascularization", Gene Therapy, pp. 1-7 (2008).
Vaknin-Dembinsky A et al: "II-23 1s Increased in Dendritic Cells in Multiple Sclerosis and Down-Regulation of IL-23 by Antisense Oligos Increases Dendritic Cell IL-10 Production", The Journal of Immunology, vol. 176, No. 12, Jun. 15, 2006, pp. 7768-7774, XP002614298.
Parham C et al: "A Receptor for the Heterodimeric Cytokine IL-23 Is Composed of IL-12R1 and a Novel Cytokine Receptor Subunit, IL-23R", The Journal of Immunology, The American Association of Immunologists, US, vol. 168, Jan. 1, 2002 (Jan. 1, 2002), pp. 5699-5708, XP002903121, ISSN: 0022-1767.
Yago Toru et al: "IL-23 induces human osteoclastogenesis via IL-17 in vitro, and anti-IL-23 antibody attenuates collagen-induced arthritis in rats", Arthritis Research and Therapy, Biomed Central, London, GB, vol. 9 , No. 5, Sep. 23, 2007 (Sep. 23, 2007). p. R96, XP021041137, ISSN: 1478-6354.

(Continued)

*Primary Examiner* — Dong Jiang
(74) *Attorney, Agent, or Firm* — Morrison & Foerster LLP

(57) ABSTRACT

Fusion proteins including an IL-17 receptor with a multimerization domain, or an IL-23 receptor and a multimerization domain, and recombinant viral vectors encoding such fusions, are described. The fusion proteins and vectors encoding such fusions, alone or in combination, can be used in methods for modulating the IL-17 and IL-23 signaling pathways and for treating or preventing diseases mediated by interleukin-17 and interleukin-23, such as immune-related and inflammatory diseases.

1 Claim, 18 Drawing Sheets

Specification includes a Sequence Listing.

(56) References Cited

OTHER PUBLICATIONS

Honjo et al., "Cloning and Complete Nucleotide Sequence of Mouse Immunoglobulin γ1 Chain Gene," Cell, 18:559-568 (1979).
Gaffen, "Structure and Signalling in the IL-17 Receptor Family," Nature Reviews Immunology, 9(8):556-567 (2009).
Forlow, "Increased Granulopoiesis Through Interleukin-17 and Granulocyte Colony-Stimulating Factor in Leukocyte Adhesion Molecule-Deficient Mice," Blood, 98(12):3309-3314 (2001).
Peppel, et al., "A Tumor Necrosis Factor (TNF) Receptor IgG Heavy Chain Chimeric Protein As a Bivalent Antagonist of TNF Activity," J. Exp. Med., 174(6):1483-1489 (1991).
Ardeljan, et al., "Interleukin-17 Retinotoxicity Is Prevented by Gene Transfer of a Soluble Interleukin-17 Receptor Acting As a Cytokine Blocker: Implications for Age-Related Macular Degeneration", PLOS One, 9(4):1-10 (2014).

\* cited by examiner

```
   1      atgggggg   ccgcacgcag   cccgccgtcc   gctgtcccgg   ggccoctgct
  48      ggggctgctc ctgctgctcc   tgggcgtgct   ggcccegggt   ggcgcctccc tgcgactcct
 108      ggaccaccgg gcgctggtct   gctcccagcc   ggggctaaac   tgcacggtca agaatagtac
 168      ctgcctggat gacagctgga   ttcaccctcg   aaacctgacc   ccctcctccc caaaggacct
 228      gcagatccag ctgcactttg   cccacaccca   acaaggagac   ctgttccccg tggctcacat
 288      cgaatggaca ctgcagacag   acgccagcat   cctgtacctc   gagggtgcag agttatctgt
 348      cctgcagctg aacaccaatg   aacgttgtg    cgtcaggttt   gagtttctgt ccaaactgag
 408      gcatcaccac aggcggtggc   gttttacctt   cagccacttt   gtggttgacc ctgaccagga
 468      atatgaggtg acggttcacc   acctgccaa    gcccatccct   gatggggacc caaaccacca
 528      gtccaagaat tccttgtgc    ctgactgtga   gcacgccagg   atgaaggtaa ccacgccatg
 588      catgagctca ggcagcctgt   gggaccccaa   catcaccgtg   gagacctgg aggccacca
 648      gctgcgtgtg agcttcaccc   tgtggaacga   atctaccat    taccagatcc tgctgaccag
 708      tttccgcac  atggagaacc   acagttgctt   tgagcacatg   caccacatac ctgcgccag
 768      accagaagag ttccaccagc   gatccaacgt   cacactcact   ctacgcaacc ttaaagggtg
 828      ctgtcgccac caagtgcaga   tccagccctt   cttcagcagc   tgcctcaatg actgcctcag
 888      acactccgcg actgtttcct   gcccagaaat   gccagacact   ccagaaccaa ttccggacta
 948      catgcccctg tgggtgtact   ggttcatcac   gggcatctcc   atcctgctgg tgggctccgt
1008      catcctgctc atcgtctgca   tgacctggag   gctagctggg   cctggaagtg aaaaatacag
1068      tgatgacacc aaatacaccg   atggctgcc    tgcggctgac   ctgatcccc  caccgctgaa
1128      gccaggaag  gtctggatca   tctactcagc   cgaccacccc   ctctacgtgg acgtggtcct
1188      gaaattcgcc cagttcctgc   tcaccgcctg   cggcacggaa   gtgcccctgg acctgctgga
1248      agagcaggcc atctcggagg   caggagtcat   gacctgggtg   ggccgtcaga agcaggagat
1308      ggtggagagc aactctaaga   tcatcgtcct   gtgctccgc    ggcacgcgcg ccaagtggca
1368      ggcgctcctg ggccgggggg   cgctgtgcg    gctgcgctgc   gaccacggaa agcccgtggg
1428      ggacctgttc actgcagcca   tgaacatgat   cctccggac    ttcagaggc  cagcctgctt
1488      cggcacctac gtagtctgct   acttcagcga   ggtcagctgt   gacggcgacg tccccgacct
1548      gttcggcgcg gcgccgcggt   acccgctcat   ggacaggttc   gaggaggtgt acttccgcat
1608      ccaggacctg gagatgtccc   agccgggccg   catgcaccgc   gtagggagc  tgtcggggga
1668      caactcctg  cggagccgg    gggcaggca    gctccgcgcc   gccctggaca ggttccggga
1728      ctggcaggtc cgctgtcccg   actggttcga   atgtgagaac   ctctactcag cagatgacca
1788      ggatgccccg tccctggacg   aagaggtgtt   tgaggagcca   ctgctgcctc cgggaaccgg
1848      catcgtgaag cgggcgcccc   tggtgcgcga   gcctggctcc   caggcctgcc tggccataga
1908      cccgctggtc gggaggaag    gaggagcagc   agtggcaaag   ctggaacctc acctgcagcc
1968      ccggggtcag ccagcgcgc   agccctcca   cacctggtg    ctgccgcag aggaggggc
2028      cctggtggcc gcggtggagc   ctgggcct    ggctgacggt   gccagtcc  ggctggcact
2088      ggcggggag  ggcgaggct   gcccgctgct   gggcagcccg   ggcgctgggc gaaatagcgt
2148      cctcttcctc ccgtggacc    ccgaggactc   gcccttggc    agcagcaccc ccatgcgtc
2208      tcctgacctc cttcagagg    acgtgaggga   gcacctcgaa   ggcttgatgc tctcgctctt
2268      cgagcagagt ctgagctgcc   aggccaggg    gggctgcagt   agacccgcca tggtcctcac
2328      agacccacac acgccctacg   aggaggagca   gggcagtca    gtgcagtctg accagggcta
2388      catctccagg agctccccgc   agcccccga    gggactcacg   aaatggagg  aagaggagga
2448      agaggagcag gacccaggga   agccggcct   gccactctct   cccgaggacc tggagagcct
2508      gaggagcctc cagcggcagc   tgcttttccg   ccagctgcag   aagaactcgg gctgggacac
2568      gatggggtca gagtcagagg   ggcccagtgc   atga
```

Fig. 1A

```
  1    MGAARSPPSAVPGPLLGLLLLLLGVLAPGGASLRLLQHRALVCSQPGLNC
 51    TVKNSTCLDDSWIHPRNLTPSSPKDLQIQLHFAHTQQGDLFPVAHIRWTL
101    QTDASILYLEGAELSVLQLNTNERLCVRFEFLSKLRHHHRRWRFTFSHFV
151    VDPDQEYEVTVHHLPKPIFDGDPNHQSKNFLVFDCEHARMKVTTPCMSSG
201    SLWDPNITVETLEAHQLRVSPTLWNRSTHYQILLTSFPHMENHSCFEHMH
251    HIPAPRPEEFHQRSNVTLTLENLKGCCRHQVQIQPFFSSCLNDCLRHSAT
301    VSCPEMPDTPRPIPDYMPLWVYWFITGISILLVGSVILLIVCMTWRLAGP
351    GSEKYSDDTKYTDGLPAADLIPPPLKPRKVWIIYSADHPLYVDVVLKFAQ
401    FLLTACGTEVALDLLEEQAISEAGVMTWVGRQKQEMVESNSKIIVLCSRG
451    TRAKWQALLGRGAPVRLRCDHGKPVGDLFTAAMNMILPDFKRPACFGTYV
501    VCYFSEVSCDGDVPDLFGAAPRYPLMDRFEEVYFRIQDLEMFQPGRMHRV
551    GELSGDNYLRSPGGRQLRAALDRFRDWQVRCPDWFECENLYSADDQDAPS
601    LDEEVPEEPLLPPGTGIVKRAPLVREPGSQACLAIDPLVGEEGAAVAKL
651    EPHLQPRGQPAPQPLHTLVLAAEEGALVAAVEPGPLADGAAVRLALAGEG
701    EACPLLGSPGAGRNSVLFLPVDPEDSPLGSSTPMASPDLLPEDVREHLEG
751    LMLSLFEQSLSCQACGGCSRPAMVLTDPHTPYEEEQRQSVQSDQGYISRS
801    SPQPPEGLTEMEEEEEEQDPGKPALPLSPEDLESLRSLQRQLLFRQLQK
851    NSGWDTMGSESEGPSA
```

Fig. 1B

```
   1       atgaa tcaggtcact attcaatggg atgcagtaat
  36 agccctttac atactcttca gctggtgtca tggaggaatt acaaatataa actgctctgg
  96 ccacatctgg gtagaaccag ccacaatttt taagatgggt atgaatatct ctatatattg
 156 ccaagcagca attaagaact gccaaccaag gaaacttcat ttttataaaa atggcatcaa
 216 agaaagattt caaatcacaa ggattaataa aacaacagct cggctttggt ataaaaactt
 276 tctggaacca catgcttcta tgtactgcac tgctgaatgt cccaaacatt ttcaagagac
 336 actgatatgt ggaaaagaca tttcttctgg atatccgcca gatattcctg atgaagtaac
 396 ctgtgtcatt tatgaatatt caggcaacat gacttgcacc tggaatgctg ggaagctcac
 456 ctacatagac acaaaatacg tggtacatgt gaagagttta gagacagaag aagagcaaca
 516 gtatctcacc tcaagctata ttaacatctc cactgattca ttacaaggtg gcaagaagta
 576 cttggtttgg gtccaagcag caaacgcact aggcatggaa gagtcaaaac aactgcaaat
 636 tcacctggat gatatagtga taccttctgc agccgtcatt tccagggctg agactataaa
 696 tgctacagtg cccaagacca taatttattg ggatagtcaa acaacaattg aaaaggtttc
 756 ctgtgaaatg agatacaagg ctacaacaaa ccaaacttgg aatgttaaag aatttgacac
 816 caattttaca tatgtgcaac agtcagaatt ctacttggag ccaaacatta gtacgtatt
 876 tcaagtgaga tgtcaagaaa caggcaaaag gtactggcag cctggagtt cactgttttt
 936 tcataaaaca cctgaaacag ttccccaggt cacatcaaaa gcattccaac atgacacatg
 996 gaattctggg ctaacagttg cttccatctc tacagggcac cttacttctg acaacagagg
1056 agacattgga cttttattgg gaatgatcgt ctttgctgtt atgttgtcaa ttcttctctt
1116 gattgggata tttaacagat cattccgaac tgggattaaa agaaggatct tattgttaat
1176 accaagtgg ctttatgaag atattcctaa tatgaaaaac agcaatgttg tgaaaatgct
1236 acaggaaaat agtgaactta tgaataataa ttccagtgag caggtcctat atgttgatcc
1296 catgattaca gagataaaag aaatcttcat cccagaacac aagcctacag actacaagaa
1356 ggagaataca ggaccctgg acaagaga ctacccgcaa aactgctat tgacaatac
1416 tacagttgta tatattcctg atctcaacac tggatataaa cccaaatttt caaatttct
1476 gctgaggga agccatctca gcaataataa tgaaattact tccttaacac ttaaaccacc
1536 agttgattcc ttagactcag gaaataatcc caggttacaa aagcatccta attttgcttt
1596 ttctgtttca agtgtgaatt cactaagcaa cacaatatttt cttggagaat taagcctcat
1656 attaaatcaa ggagaatgca gttctctga catacaaaac tcagtagagg aggaaaccac
1716 catgctttg gaaatgatt cacccagtga actattcca gaacagaccc tgcttcctga
1776 tgaatttgtc tcctgtttgg ggatcgtgaa tgaggagttg ccatctatta atacttattt
1836 tccacaaaat attttggaaa gccacttcaa taggatttca ctcttggaaa agtag
```

Fig. 2A

```
  1  MNQVTIQWDAVIALYILFSWCRGGITNINCSGHIWVEPATIFKMGMNISI
 51  YCQAAIKNCQPRKLHFYKNGIKERFQITRINKTTARLWYKNFLEPHASMY
101  CTAECPKHFQETLICGKDISSGYPPDIPDEVTCVIYEYSGNMTCTWNAGK
151  LTYIDTKYVVSVKSLETEEEQQYLTSSYINISTDSLQGGKKYLVWVQAAN
201  ALGMERSKQLQIHLDDIVIPSAAVISRAETINATVPKTIIYWDSQTTIEK
251  VSCEMRYKATTNQTWNVKEFDTNFTYVQQSEFYLEPNIKYVFQVRCQETG
301  KRYWQPWSSLFFRKTPETVPQVTSKAFQHDTWNSGLTVASISTGHLTSDN
351  RGDIGLLLGMIVFAVMLSILSLIGIFNRSFRTGIKRRILLLIPKWLYEDI
401  PNMKNSNVVKMLQENSELMNNNSSEQVLYVDPMITEIKEIFIPEHKPTDY
451  KKENTGPLETRDYPQNSLFDNTTVVYIPDLNTGYKPQISNFLPEGSHLSN
501  NNEITSLTLKPPVDSLDSGNNPRLQKHPNFAFSVSSVNSLSNTIFLGELS
551  LILNQGECSSPDIQNSVEEETTMLLENDSPSETIPEQTLLPDEFVSCLGI
601  VNEELPSINTYFPQNILESHFNRISLLEK
```

Fig. 2B

```
1     ATGAATCATGTCACTATTCAATGGGATGCAGTAATAGCCCTTTACATACTCTTCAGCTGG
61    TGTCATGGAGGAATTACAAATATAAACTGCTCTGGCCACATCTGGGTAGAACCAGCCACA
121   ATTTTTAAGATGGGTATGAATATCTCTATATATTGCCAAGCAGCAATTAAGAACTGCCAA
181   CCAAGGAAACTTCATTTTTATAAAAATGGCATCAAAGAAAGATTTCAAATCACAAGGATT
241   AATAAAACAACAGCTCGGCTTTGGTATAAAAACTTTCTGGAACCACATGCTTCTATGTAC
301   TGCACTGCTGAATGTCCCAAACATTTTCAAGAGACACTGATATGTGGAAAAGACATTTCT
361   TCTGGATATCCGCCAGATATTCCTGATGAAGTAACCTGTGTCATTTATGAATATTCAGGC
421   AACATGACTTGCACCTGGAATGCTGGGAAGCTCACCTACATAGACACAAAATACGTGGTA
481   CATGTGAAGAGTTTAGAGACAGAAGAAGAGCAACAGTATCTCACCTCAAGCTATATTAAC
541   ATCTCCACTGATTCATTACAAGGTGGCAAGAAGTACTTGGTTTGGGTCCAAGCAGCAAAC
601   GCACTAGGCATGGAAGAGTCAAAACAACTGCAAATTCACCTGGATGATATAGTGATACCT
661   TCTGCAGCCGTCATTTCCAGGGCTGAGACTATAAATGCTACAGTGCCCAAGACCATAATT
721   TATTGGGATAGTCAAACAACAATTGAAAAGGTTTCCTGTGAAATGAGATACAAGGCTACA
781   ACAAACCAAACTTGGAATGTTAAAGAATTTGACACCAATTTTACATATGTGCAACAGTCA
841   GAATTCTACTTGGAGCCAAACATTAAGTACGTATTTCAAGTGAGATGTCAAGAAACAGGC
901   AAAAGGTACTGGCAGCCTTGGAGTTCACCGTTTTTTCATAAAAACACCTGAAACAGTTCCC
961   CAGGTCACATCAAAAGCATTCCAACATGACACATGGAATTCTGGGCTAACAGTTGCTTCC
1021  ATCTCTACAGGGCACCTTACCGGTGGAGGTGGAGGTGGAGGTGGAGGTCAGCCCCGAGAA
1081  CCACAGGTGTACACCCTGCCCCCATCCCGGGATGAGCTGACCAAGAACCAGGTCAGCCTG
1141  ACCTGCCTGGTCAAAGGCTTCTATCCCAGCGACATCGCCGTGGAGTGGGAGAGCAATGGG
1201  CAGCCGGAGAACAACTACAAGACCACGCCTCCCGTGCTGGACTCCGACGGCTCCTTCTTC
1261  CTCTACAGCAAGCTCACCGTGGACAAGAGCAGGTGGCAGCAGGGGAACGTCTTCTCATGC
1321  TCCGTGATGCATGAGGCTCTGCACAACCACTACACGCAGAAGAGCCTCTCCCTGTCTCCG
1381  GGTAAATAG
```

Fig. 5A

```
1     MNHVTIQWDAVIALYILFSWCHGGITNINCSGHIWVEPATIFKMGMNISI
51    YCQAAIKNCQPRKLHFYKNGIKERFQITRINKTTARLWYKNFLEPHASMY
101   CTAECPKHFQETLICGKDISSGYPPDIPDEVTCVIYEYSGNMTCTWNAGK
151   LTYIDTKYVVHVKSLETEEEQQYLTSSYINISTDSLQGGKKYLVWVQAAN
201   ALGMEESKQLQIHLDDIVIPSAAVISRAETINATVPKTIIYWDSQTTIEK
251   VSCEMRYKATTNQTWNVKEFDTNFTYVQQSEFYLEPNIKYVFQVRCQETG
301   KRYWQPWSSPFFHKTPETVPQVTSKAFQHDTWNSGLTVASISTGHLTGGG
351   GGGGGQPREPQVYTLPPSRDELTKNQVSLTCLVKGFYPSDIAVEWESNG
401   QPENNYKTTPPVLDSDGSFFLYSKLTVDKSRWQQGNVFSCSVMHEALHNH
451   YTQKSLSLSPGK
```

Fig. 5B

```
1     ATGGGGGCCGCACGCAGCCCGCCGTCCGCTGTCCGGGGCCCCTGCTGGGGCTGCTCCTG
61    CTGCTCCTGGGCGTGCTGGCCCCGGGTGGCGCCTCCCTGCGACTCCTGGACCACCGGGCG
121   CTGGTCTGCTCCCAGCCGGGGCTAAACTGCACGGTCAAGAATAGTACCTGCCTGGATGAC
181   AGCTGGATTCACCCTCGAAACCTGACCCCCTCCTCCCCAAAGGACCTGCAGATCCAGCTG
241   CACTTTGCCCACACCCAACAAGGAGACCTGTTCCCCGTGGCTCACATCGAATGGACACTG
301   CAGACAGACGCCAGCATCCTGTACCTCGAGGGTGCAGAGTTATCTGTCCTGCAGCTGAAC
361   ACCAATGAACGTTTGTGCGTCAGGTTTGAGTTTCTGTCCAAACTGAGGCATCACCACAGG
421   CGGTGGCGTTTTACCTTCAGCCACTTTGTGGTTGACCCTGACCAGGAATATGAGGTGACC
481   GTTCACCACCTGCCCAAGCCCATCCCTGATGGGGACCCAAACCACCAGTCCAAGAATTTC
541   CTTGTGCCTGACTGTGAGCACGCCAGGATGAAGGTAACCACGCCATGCATGAGCTCAGGC
601   AGCCTGTGGGACCCCAACATCACCGTGGAGACCCTGGAGGCCCACCAGCTGCGTGTGAGC
661   TTCACCCTGTGGAACGAATCTACCCATTACCAGATCCTGCTGACCAGTTTTCCGCACATG
721   GAGAACCACAGTTGCTTTGAGCACATGCACCACATACCTGCGCCCAGACCAGAAGAGTTC
781   CACCAGCGATCCAACGTCACACTCACTCTACGCAACCTTAAAGGGTGCTGTCGCCACCAA
841   GTGCAGATCCAGCCCTTCTTCAGCAGCTGCCTCAATGACTGCCTCAGACACTCCGCGACT
901   GTTTCCTGCCCAGAAATGCCAGACACTCCAGAACCAATTCCGGACTACATGACCGGTGGA
961   GGTGGAGGTGGAGGTGGAGGTCAGCCCCGAGAACCACAGGTGTACACCCTGCCCCCATCC
1021  CGGGATGAGCTGACCAAGAACCAGGTCAGCCTGACCTGCCTGGTCAAAGGCTTCTATCCC
1081  AGCGACATCGCCGTGGAGTGGGAGAGCAATGGGCAGCCGGAGAACAACTACAAGACCACG
1141  CCTCCCGTGCTGGACTCCGACGGCTCCTTCTTCCTCTACAGCAAGCTCACCGTGGACAAG
1201  AGCAGGTGGCAGCAGGGGAACGTCTTCTCATGCTCCGTGATGCATGAGGCTCTGCACAAC
1261  CACTACACGCAGAAGAGCCTCTCCCTGTCTCCGGGTAAATAG
```

Fig. 6A

```
1     MGAARSPPSAVPGPLLGLLLLLLGVLAPGGASLRLLDHRRALVCSQPGLNC
51    TVKNSTCLDDSWIHPRNLTPSSPKDLQIQLHFAHTQQGDLFPVAHIEWTL
101   QTDASILYLEGAELSVLQLNTNERLCVRFEFLSKLRHHHRRWRFTFSHFV
151   VDPDQEYEVTVHHLPKPIPDGDPNHQSKNFLVPDCEHARMKVTTPCMSSG
201   SLWDPNITVETLEAHQLRVSFTLWNESTHYQILLTSFPHMENHSCFEHMH
251   HIPAPRPEEFHQRSNVTLTLRNLKGCCRHQVQIQPFFSSCLNDCLRHSAT
301   VSCPEMPDTPEPIPDYMTGGGGGGGGQPREPQVYTLPPSRDELTKNQVS
351   LTCLVKGFYPSDIAVEWESNGQPENNYKTTPPVLDSDGSFFLYSKLTVDK
401   SRWQQGNVFSCSVMHEALHNHYTQKSLSLSPGK
```

Fig. 6B

FUSION PROTEINS AND METHODS FOR INHIBITING IL-17 PATHWAYS

CROSS-REFERENCE TO RELATED APPLICATION

This application claims the benefit under 35 USC § 119(e)(1) of U.S. Provisional Application No. 60/974,892, filed Sep. 25, 2007, which application is incorporated herein by reference in its entirety.

TECHNICAL FIELD

The present invention relates generally to compositions and methods for modulating interleukin pathways. In particular, the present invention pertains to compositions and methods for inhibiting IL-17 and IL-23 signaling pathways and for treating or preventing diseases mediated by interleukin-17 and interleukin-23, such as immune-related and inflammatory diseases.

BACKGROUND

Immune related and inflammatory diseases are often caused by multiple interconnected biological pathways which in the normal state respond to injury, initiate repair from injury, and mount innate and acquired immune defenses against foreign organisms. Disease or pathology occurs when these normal physiological pathways cause additional injury either directly related to the intensity of the response, as a consequence of abnormal regulation or excessive stimulation, as a reaction to self, or a combination of these factors.

Although the genesis of these diseases often involves multistep pathways and multiple biological systems and pathways, intervention at critical points in one or more of these pathways can have an ameliorative or therapeutic effect. Therapeutic intervention can occur by either antagonizing a detrimental process or pathway, or by stimulating a beneficial process or pathway.

Many immune related diseases are known and have been extensively studied. Such diseases include immune-mediated inflammatory diseases, such as rheumatoid arthritis, osteoarthritis, uveitis, multiple sclerosis, type 1 diabetes, immune mediated renal disease, hepatobiliary diseases, inflammatory bowel disease (IBD), psoriasis, and asthma; non-immune-mediated inflammatory diseases; infectious diseases; immunodeficiency diseases; neoplasia, induction of transplantation tolerance and the like.

Members of the interleukin family have been shown to be related to immune-mediated and inflammatory disease. For example, interleukin-23 (IL-23) has been shown to drive a pathogenic T-cell population that induces autoimmune inflammation. The IL-23 pathway has been implicated as a driving factor in a variety of immune-mediated diseases, including inflammatory bowel disease, rheumatoid arthritis, experimental autoimmune encephalomyelitis, cancer, and type 1 diabetes. IL-23 uses many of the same signal-transduction components as IL-12, including IL-12Rß1, Janus kinase 2, Tyk2, signal transducer and activator of transcription (Stat)1, Stat3, Stat4, and Stat5. IL-23 promotes cellular immunity by inducing interferon-γ production and proliferative responses in target cells. Additionally, IL-23 promotes the T helper cell type 1 costimulatory function of antigen-presenting cells. IL-23 preferentially acts on memory $CD4^+$ T cells.

IL-23 also appears to have an important function in the control of certain intracellular infections, including those caused by *Cryptococcus* (Decken et al., *Infect. Immun.* (1998) 66:4994-5000); *Salmonella* (Lehmann et al., *J. Immunol.* (2001) 167:5304-5315): *Francisella* (Elkins et al., *Infect. Immun.* (2002) 70:1936-1948); and mycobacteria (Holscher et al., *J. Immunol.* (2001) 167:6957-6966; Cooper et al., *J. Immunol.* (2002) 168:1322-1327). Additionally, these studies indicate a role for IL-23 in the alloreactive $T_H1$ responses in transplant models (Piccotti et al., *J. Immunol.* (1998) 160:1132-1138)

IL-23 exists as a heterodimer that includes the IL-12 p40 and IL-23-specific p19 subunits. IL-23 binds the IL-23 receptor complex, composed of IL-23r and IL-12rß1 (Parham et al., *J. Immunol.* (2002) 168:5699-5708). Upon engaging IL-23, IL-12rß1 and IL-23r associate, marking the beginning of the IL-23 signal-transduction cascade.

The human IL-23 receptor is a 629 amino acid type I transmembrane protein, with sequence homology with IL-12rß2 and gp130. A functional murine IL-23 receptor has also been discovered, based on its homology with the human IL-23r gene sequence. The murine counterpart of the human IL-23 receptor is 644 amino acids in length and has 84% sequence homology with the protein-coding regions of the human IL-23 receptor gene (Parham et al., *J. Immunol.* (2002) 168:5699-5708).

Structurally, the human IL-23 receptor includes a signal sequence, an immunoglobulin-like domain, and two cytokine receptor domains. The sequence motif, WQPWS, is present in the membrane-transmembrane proximal cytokine receptor domain, likely corresponding to the WSXWS signature motif characteristic of cytokine receptors. The cytoplasmic portion of the human IL-23 receptor has 252 amino acids, including seven tyrosine residues. Protein sequence analysis of this cytoplasmic portion shows three potential Src homology 2 domain-binding sites and two potential Stat-binding sites. These sites display 100% amino acid identity to the mouse and human IL-23 receptor proteins within these motifs (Parham et al., *J. Immunol.* (2002) 168:5699-5708).

Interleukin 17 (IL-17) is a homodimeric proinflammatory cytokine of about 32 kDa which is synthesized and secreted by $CD4^+$ activated memory T-lymphocytes. IL-17 acts to induce proinflammatory responses in a wide variety of peripheral tissues. It is a potent inducer of the maturation of $CD34^+$ hematopoietic precursors into neutrophils. IL-17 plays a pathogenic role in many inflammatory and autoimmune diseases such as rheumatoid arthritis, osteoarthritis, asthma, uveitis, type 1 diabetes and multiple sclerosis.

IL-17 has been found to stimulate the production of several cytokines. For example, it induces the secretion of IL-6, IL-8, prostaglandin E2, MCP-1 and G-CSF by adherent cells such as fibroblasts, keratinocytes, epithelial and endothelial cells. IL-17 also has the ability to induce ICAM-1 surface expression, proliferation of T-cells, and growth and differentiation of $CD34^+$ human progenitors into neutrophils. IL-17 has also been implicated in bone metabolism, and may play an important role in pathological conditions characterized by the presence of activated T-cells and TNF-α production such as rheumatoid arthritis and loosening of bone implants (Van Bezooijen et al., *J. Bone Miner. Res.* (1999) 14:1513-1521). Activated T-cells of synovial tissue derived from rheumatoid arthritis patients have been found to secrete higher amounts of IL-17 than those derived from normal individuals or osteoarthritis patients (Chabaud et al., *Arthritis Rheum.* (1999) 42:963-970). IL-17 may actively contribute to synovial inflammation in rheumatoid arthritis.

IL-17 appears to contribute to the pathology of rheumatoid arthritis and osteoarthritis by a mechanism in addition to its proinflammatory role. For example, IL-17 has been shown to induce the expression of osteoclast differentiation factor (ODF) mRNA in osteoblasts (Kotake et al., *J. Clin. Invest.* (1999) 103:1345-1352). ODF stimulates differentiation of progenitor cells into osteoclasts which are involved in bone resorption. Since the level of IL-17 is significantly increased in synovial fluid of rheumatoid arthritis patients, it appears that IL-17-induced osteoclast formation plays a crucial role in bone resorption in rheumatoid arthritis. IL-17 is also believed to play a key role in certain other autoimmune disorders such as multiple sclerosis (Matusevicius et al., *Mult. Scler.* (1999) 5:101-104).

IL-17 also shares sequence similarity with mammalian cytokine-like factor 7 that is involved in bone and cartilage growth. Other proteins with which IL-17 polypeptides share sequence similarity are human embryo-derived interleukin-related factor (EDIRF) and interleukin-20.

Consistent with the wide-range of activities demonstrated by IL-17, the cell surface receptor for IL-17 is widely expressed in many tissues and cell types (Yao et al., *Cytokine* (1997) 9:794). The human IL-17 receptor is 866 amino acids in length and includes a single transmembrane domain and a long, 525 amino acid, intracellular domain. The receptor sequence is unique and is not similar to that of any of the receptors from the cytokine/growth factor receptor family.

It has been demonstrated that IL-17 activity is mediated through binding to its unique cell surface receptor. Studies have shown that contacting T-cells with a soluble form of the IL-17 receptor polypeptide inhibits T-cell proliferation and IL-2 production induced by PHA, concanavalin A and anti-TCR monoclonal antibody (Yao et al., *J. Immunol.* (1995) 155:5483-5486).

SUMMARY OF THE INVENTION

The present invention is based on the surprising discovery that interleukin pathways can be successfully modulated by delivering interleukin receptor constructs. Multimeric constructs including interleukin receptors and an immunoglobulin constant region multimerization domain and/or proteins expressed from such multimeric constructs, successfully bind to and neutralize their corresponding ligands.

This novel therapy approach for the delivery of IL-17 and IL-23 receptor constructs or proteins expressed from such constructs provides a highly desirable method for modulating the activity of the IL-17 and IL-23 signaling pathways, and for treating and preventing diseases related thereto.

Thus in one embodiment, the invention is directed to a recombinant virus comprising a polynucleotide encoding a fusion protein, wherein the fusion protein comprises (a) an interleukin receptor selected from the group consisting of an IL-17 receptor and an IL-23 receptor wherein the IL-23 receptor lacks an IL-12 receptor component; and (b) an immunoglobulin constant region multimerization domain, wherein when the fusion protein is expressed, a multimer of the fusion protein is produced. In certain embodiments, the multimer is a homodimer. In additional embodiments, the interleukin receptor is a soluble interleukin receptor.

In further embodiments, the multimerization domain comprises the CH3 domain of an IgG, or an active fragment thereof and the multimerization domain is from an IgG1, an IgG2, an IgG3 or an IgG4, such as from the constant region of an IgG1 heavy chain.

In additional embodiments, the fusion protein comprises the amino acid sequence of FIG. 5B (SEQ ID NO:6), or an active variant thereof having at least 90% sequence identity to the sequence of FIG. 5B (SEQ ID NO:6), or the fusion protein comprises the amino acid sequence of FIG. 6B (SEQ ID NO:8), or an active variant thereof having at least 90% sequence identity to the sequence of FIG. 6B (SEQ ID NO:8).

In additional embodiments, the recombinant virus is a recombinant adenovirus or a recombinant adeno-associated virus virion.

In further embodiments, the invention is directed to a kit comprising the recombinant viruses described above, and instructions for transducing a host cell with the recombinant virus.

In additional embodiments, the invention is directed to a method of inhibiting an interleukin pathway selected from the group consisting of an IL-23 pathway and an IL-17 pathway. The method comprises administering a recombinant virus as described above to a cell to transduce the cell. In certain embodiments, the recombinant virus is administered to cells in vitro. The transduced cells can further be administered to a subject in need thereof. In other embodiments, the recombinant virus is administered to cells in vivo in a subject in need thereof.

In further embodiments, the invention is directed to a fusion protein selected from the group consisting of a protein comprising the sequence of amino acids of FIG. 5B (SEQ ID NO:6), or a sequence of amino acids with at least 90% sequence identity thereto, and a protein comprising the sequence of amino acids of FIG. 6B (SEQ ID NO:8), or a sequence of amino acids with at least 90% sequence identity thereto.

In additional embodiments, the invention is directed to a polynucleotide encoding the fusion proteins above, as well as recombinant vectors comprising (a) the polynucleotide and (b) at least one control element operably linked to said polynucleotide, whereby said coding sequence can be transcribed and translated in a host cell. In further embodiments, the invention is directed to a host cell comprising the recombinant vector, as well as methods for producing a fusion protein, comprising culturing a population of the host cells under conditions for producing the protein.

In yet additional embodiments, the invention is directed to a method of inhibiting an interleukin pathway selected from the group consisting of an IL-23 pathway and an IL-17 pathway, the method comprising administering a fusion protein, or a polynucleotide encoding the fusion protein, as described above, to a subject in need thereof.

In certain embodiments, a polynucleotide as described above is administered to a cell to transduce the cell. The polynucleotide can be administered to cells in vitro and the transduced cells can be further administered to a subject in need thereof. Alternatively, the polynucleotide is administered to cells in vivo in a subject in need thereof.

In further embodiments, the subject is administered both a polynucleotide encoding the fusion protein and the fusion protein. The fusion protein can be administered prior to, subsequent to, or concurrently with the polynucleotide.

These and other embodiments of the subject invention will readily occur to those of skill in the art in view of the disclosure herein.

BRIEF DESCRIPTION OF THE FIGURES

FIGS. 1A-1B (SEQ ID NOS:1 and 2) show the full-length nucleotide sequence (FIG. 1A) and corresponding amino acid sequence (FIG. 1B) of a representative human IL-17r.

FIGS. 2A-2B (SEQ ID NOS:3 and 4) show the full-length nucleotide sequence (FIG. 2A) and corresponding amino acid sequence (FIG. 2B) of a representative human IL-23r.

FIGS. 5A and 5B (SEQ ID NOS:5 and 6) show the nucleotide sequence and corresponding amino acid sequence of the sIL23R-9gly-CH3 construct depicted in FIG. 3.

FIGS. 6A and 6B (SEQ ID NOS:7 and 8) show the nucleotide sequence and corresponding amino acid sequence of the sIL17RA-9gly-CH3 construct depicted in FIG. 4.

DETAILED DESCRIPTION OF THE INVENTION

Figure 3:
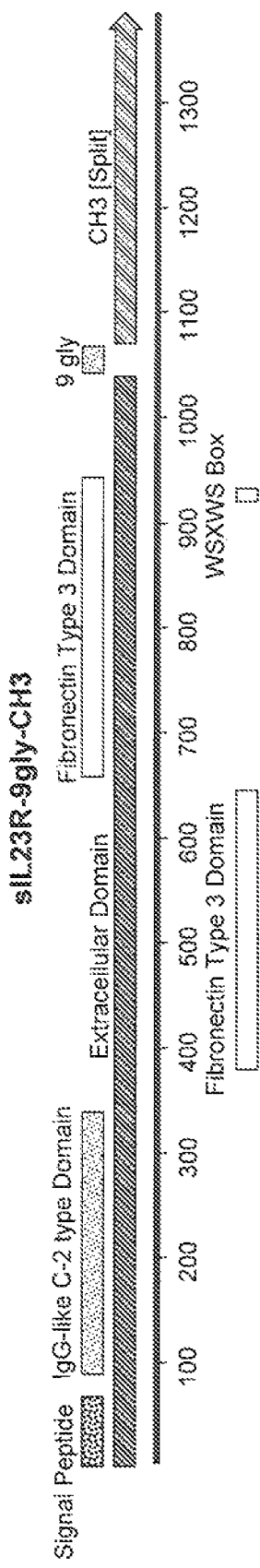
FIG. 3 is a diagrammatic representation of a fusion construct including a soluble IL-23r linked to the CH3 domain of the Fc region of a human IgG1 immunoglobulin via a linker of nine Gly residues (sIL23R-9gly-CH3).

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an interleukin receptor" includes a mixture of two or more such receptors, and the like.

The terms "interleukin-17 receptor" (IL-17r) and "interleukin-23 receptor" (IL-23r) or a nucleotide sequence encoding the same, refer to a protein or nucleotide sequence, respectively, that is derived from any IL-17 receptor and IL-23 receptor, respectively, regardless of source. The terms, as used herein, refer to molecules capable of binding to and modulating activity of the corresponding ligand, as measured in any of the known IL-17 and IL-23 activity tests, including those described further herein, such as by reducing or inhibiting the production of IL-17 and IL-23, respectively. The full-length nucleotide sequence and corresponding amino acid sequence of a representative human IL-17r is shown in FIGS. 1A-1B (SEQ ID NOS:1 and 2) and the full-length nucleotide sequence and corresponding amino acid sequence of a representative human IL-23r is shown in FIGS. 2A-2B (SEQ ID NOS:3 and 4). However, an interleukin receptor as defined herein is not limited to the depicted sequences as several such receptors are known and variations in these receptors will occur between species.

The full-length proteins, with or without the signal sequence, and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70 . . . 80 . . . 85 . . . 90 . . . 95 . . . 98 . . . 99% etc. identity that retain the ability to modulate activity of the corresponding ligand, are contemplated for use herein.

A "native" polypeptide, such as an interleukin receptor sequence, refers to a polypeptide having the same amino acid sequence as the corresponding molecule derived from nature. Such native sequences can be isolated from nature or can be produced by recombinant or synthetic means. The term "native" sequence specifically encompasses naturally-occurring truncated or secreted forms of the specific molecule (e.g., an extracellular domain sequence), naturally-occurring variant forms (e.g., alternatively spliced forms) and naturally-occurring allelic variants of the polypeptide. In various embodiments of the invention, the native molecules disclosed herein are mature or full-length native sequences comprising the full-length amino acids sequences shown in the accompanying figures. However, while some of the molecules disclosed in the accompanying figures begin with methionine residues designated as amino acid position 1 in the figures, other methionine residues located either upstream or downstream from amino acid position 1 in the figures may be employed as the starting amino acid residue for the particular molecule. Alternatively, depending on the expression system used, the molecules described herein may lack an N-terminal methionine.

By "extracellular domain" is meant a form of the receptor polypeptide which includes all or a fragment of the extracellular domain and lacks all or a portion of the transmembrane domain and may also be devoid of the cytoplasmic domain. Typically, when used in the present invention, the extracellular domain is essentially free of both the transmembrane and cytoplasmic domains. Ordinarily, an extracellular domain includes less than 10% of such transmembrane and/or cytoplasmic domains, preferably less than 5% of these domains, preferably, less than 1%, and even more preferably, less than 0.5% of such domains. Transmembrane domains for the receptors described herein can be identified pursuant to criteria routinely employed in the art for identifying hydrophobic domains, for example, using standard hydropathy plots, such as those calculated using the Kyte-Doolittle technique, Kyte et al., *J. Mol. Biol.* (1982) 157:105-132.

As explained above, the interleukin receptors for use with the present invention may or may not include the native signal sequence. The approximate location of the signal peptides of the interleukin receptors described herein are described in the specification and in the accompanying figures. It is noted, however, that the C-terminal boundary of a signal peptide may vary, typically by no more than about 5 amino acids on either side of the signal peptide C-terminal boundary as described herein. The C-terminal boundary of the signal peptide may be identified pursuant to criteria routinely employed in the art, such as described in Nielsen et al., *Prot. Eng.* (1997) 10:1-6 and von Heinje et al., *Nucl. Acids. Res*. (1986) 14:4683-4690. Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

By "variant" is meant an active polypeptide as defined herein having at least about 80% amino acid sequence identity with the corresponding full-length native sequence, a polypeptide lacking the signal peptide, an extracellular domain of a polypeptide, with or without a signal peptide, or any other fragment of a full-length polypeptide sequence as disclosed herein. Such polypeptide variants include, for instance, polypeptides wherein one or more amino acid residues are added, or deleted, at the N- and/or C-terminus of the full-length native amino acid sequence. Ordinarily, a variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to the corresponding full-length native sequence. Ordinarily, variant polypeptides are at least about 10 amino acids in length, such as at least about 20 amino acids i+n length, e.g., at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

Particularly preferred variants include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively.

Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vivo.

By "recombinant virus" is meant a virus that has been genetically altered, e.g., by the addition or insertion of a heterologous nucleic acid construct into the particle.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "multimerization domain" as used in the context of the present invention, is meant to refer to the portion of the molecule to which the interleukin receptor is joined, either directly or through a "linker domain." The multimerization domain is preferably a polypeptide domain which facilitates the interaction of two or more multimerization domains and/or interleukin receptor domains. Homodimers result from the pairing or crosslinking of two monomers comprising an interleukin receptor and a multimerization domain.

For example, a multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in, for example, U.S. Pat. No. 5,731,168, incorporated herein by reference in its entirety. Protuberances are constructed by, e.g., replacing small amino acid side chains from the interface of a first polypeptide with a larger side chain (for example a tyrosine or tryptophan). Compensatory cavities of identical or similar size to the protuberances are optionally created on the interface of a second polypeptide by replacing large amino acid side chains with smaller ones (for example alanine or threonine).

Therefore, in a preferred aspect, the multimerization domain provides that portion of the molecule which promotes or allows the formation of dimers, trimers, and the like from monomeric domains. Preferably, multimerization domains are immunoglobulin constant region domains.

"Immunoglobulins" (Igs) are proteins, generally glycoproteins, that are antibodies or antibody-like molecules which lack antigen specificity. Immunoglobulins are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has an amino (N) terminal variable domain (VH) followed by carboxy (C) terminal constant domains. Each light chain has a variable N-terminal domain (VL) and a C-terminal constant domain; the constant domain of the light chain (CL) is aligned with the first constant domain (CH1) of the heavy chain, and the light chain variable domain is aligned with the variable domain of the heavy chain. According to the domain definition of immunoglobulin polypeptide chains, light (L) chains have two conformationally similar domains VL and CL; and heavy chains have four domains (VH, CH1, CH2, and CH3) each of which has one intrachain disulfide bridge.

Depending on the amino acid sequence of the constant (C) domain of the heavy chains, immunoglobulins can be assigned to different classes. There are five major classes of immunoglobulins: IgA, IgD, IgE, IgG, and IgM. The immunoglobulin class can be further divided into subclasses (isotypes), e.g., IgG1, IgG2, IgG3, IgG4, IgG5, IgA1, and IgA2. Each heavy chain has at one end a variable domain (VH) followed by a number of constant domains. The light chains of antibodies from any vertebrate species can be assigned to one of two distinct types called kappa (K) or lambda (λ), based upon the amino acid sequence of their constant domains.

The term "Fc region" refers to the C-terminal (constant) region of an immunoglobulin heavy chain. The Fc region may be a native sequence Fc region or a variant Fc region. Although the boundaries of the Fc region of an immunoglobulin heavy chain may vary, the human IgG heavy chain Fc region typically stretches from an amino acid residue at position Cys226, or from Pro230, to the carboxyl-terminus of a full-length human IgG1. The Fc region of an immunoglobulin generally comprises two constant domains, CH2 and CH3. The last residue, lysine, in the heavy chain of IgG1 can but need not be present as the terminal residue in the Fc in the mature protein. One human IgG1 heavy chain Fc region is defined in NCBI accession number P01857.

The "CH2 domain" of a human IgG Fc region (also referred to as "Cγ2" domain) usually extends from about amino acid 231 to about amino acid 340 of a full-length IgG, but from Pro111 to Lys223 of the human IgG heavy chain Fc region.

The "CH3 domain" comprises the residues C-terminal to a CH2 domain in a human IgG1 Fc region (i.e. from about amino acid residue 341 to about amino acid residue 447 of a full-length IgG, but from Gly224 to Lys330 of a human IgG heavy chain Fc region).

The "hinge region" is generally defined as stretching from Glu216 to Pro230 of a full-length human IgG1 (Burton, *Molec. immunol.* (1985) 22:161-206), but from Glu99 to Pro110 of a human IgG heavy chain Fc region. Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of a full-length human IgG1.

A "native Fc region sequence" comprises an amino acid sequence identical to the amino acid sequence of an Fc region found in nature. Native human Fc region sequences include but are not limited to the human IgG1 Fc region (non-A and A allotypes); the human IgG2 Fc region; the human IgG3 Fc region; and the human IgG4 Fc region as well as naturally occurring variants thereof. Native Fc regions from other species, such as murine Fc regions, are also well known.

A "functional Fc region" possesses an "effector function" of a native Fc region. Exemplary "effector functions" include C1q binding; complement-dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions typically require the Fc region to be combined with a binding domain (i.e., an interleukin ligand herein) and can be assessed using various assays known in the art. Preferably, the Fc region is a human Fc region, e.g. a native sequence human Fc region such as a human IgG1 (A and non-A allotypes), IgG2, IgG3 or IgG4 Fc region. Such sequences are known. See, e.g., PCT Publication NO. WO01/02440, incorporated herein by reference in its entirety.

The term "modulate" means to affect (e.g., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

"Active" or "activity" for purposes of the present invention refers to forms of an interleukin receptor polypeptide which retain a biological activity (either inhibitory or stimulatory) of the corresponding native or naturally occurring polypeptide. The activity may be greater than, equal to, or less than that observed with the corresponding native or naturally occurring polypeptide. A preferred activity includes modulating the level of the IL-17 and/or IL-23 signaling pathway in a subject suffering from an immune related disease.

By "immune-related disease" is meant a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, and the like. Further examples of immune related diseases are presented below.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3-prime (3')" or "5-prime (5')" relative to another sequence, it is to be understood that it is the position of the sequences in the "sense" or "coding" strand of a DNA molecule that is being referred to as is conventional in the art.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "effective amount" or "therapeutically effective amount" of a composition or agent, as provided herein, refer to a nontoxic but sufficient amount of the composition or agent to provide the desired response, such as modulating an interleukin receptor ligand, e.g., reducing or inhibiting the production of IL-17 and IL-23 and/or treating or preventing disease related thereto. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The term "about", particularly in reference to a given quantity, is meant to encompass deviations of plus or minus five percent.

"Treatment" or "treating" a particular disease includes: (1) preventing the disease, i.e. preventing the development of the disease or causing the disease to occur with less intensity in a subject that may be exposed to or predisposed to the disease but does not yet experience or display symptoms of the disease, (2) inhibiting the disease, i.e., arresting the development or reversing the disease state, or (3) relieving symptoms of the disease i.e., decreasing the number of symptoms experienced by the subject.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that protein or gene therapy using constructs encoding interleukin receptors, and in particular the IL-17 and IL-23 receptors, serves to modulate the corresponding signaling pathways, and therefore provides a useful technique for treating and preventing immune-related disorders, such as autoimmune diseases and inflammatory conditions including joint and bone diseases. Protein and gene therapy techniques can be used alone or in combination, or in conjunction with traditional drugs.

The constructs of the present invention also provide a means for transducing cells in vitro to study the IL-17 and IL-23 signaling pathways, e.g., in order to screen for agonists and antagonists thereto.

The constructs used in the present methods encode fusion proteins that include an interleukin receptor, or an active portion thereof, linked to an immunoglobulin constant region multimerization domain, either directly or via a linker. Preferably, a soluble form, i.e., a transmembrane domain-deleted or inactivated form, of the receptor is used. The receptor can be present either upstream or downstream from the immunoglobulin region. Purified fusion protein may be prepared in vitro from the constructs. Typically, the fusion protein is produced in multimeric form when expressed in vivo. The multimer can be a dimer, trimer, etc. Generally, the interleukin receptor is present in a homodimeric form. Thus, monomers of IL-17r and IL-23r will form homodimers upon expression. Although the IL-23r normally exists as a heterodimer that includes the IL-12 p40 and IL-23-specific p19 subunits, the present invention provides for an IL-23r that lacks an IL-12 subunit. Surprisingly, this IL-23r homodimer is still able to bind its respective ligand and modulate the IL-23 pathway.

In order to further an understanding of the invention, a more detailed discussion is provided below regarding the receptor-immunoglobulin fusions, as well as various gene delivery methods for use with the present invention.

Interleukin Receptor-Immunoglobuin Fusions

As explained above, the present invention makes use of interleukin receptor-immunoglobulin fusions and/or constructs that encode such fusions to modulate the signal pathways mediated by the interleukin receptors. The interleukin receptor component of the fusions is either an IL-17 receptor (IL-17r) or an IL-23 receptor (IL-23r). The native molecules, as well as active fragments and analogs thereof, which retain the ability to bind to the corresponding ligand and modulate ligand activity, as measured in any of the various assays and animal models including those described further herein, are intended for use with the present invention.

The nucleotide and corresponding amino acid sequence for a representative full-length human IL-17r receptor is shown in FIGS. 1A and 1B, respectively (SEQ ID NOS:1 and 2, NCBI Accession No. NM_014339 and NP_055154, respectively). The full-length molecule includes 866 amino acids. Amino acids 1-31 represent a signal peptide. The signal peptide is followed by a mature peptide consisting of a 289 amino acid extracellular domain, a 21 amino acid transmembrane domain, and a 525 amino acid cytoplasmic tail. The amino acid sequence of the human IL-17r is 69% identical to the mouse IL-17r.

As explained above, the use of a soluble IL-17r is particularly preferred. A soluble IL-17r typically includes the extracellular domain or an active portion thereof but lacks the transmembrane domain and, optionally, the cytoplasmic tail and may or may not include the native or a heterologous signal sequence. One example of a soluble IL-17r comprises the signal peptide and the extracellular domain of the molecule, such as represented by residues 1 to 320 of SEQ ID NO:2, or an active fragment thereof.

As explained above, fusions between an IL-23r and an immunoglobulin molecule will also find use herein. Structurally, the IL-23 receptor includes in N-terminal to C-terminal order, a signal sequence, an immunoglobulin-like domain, two cytokine receptor domains, a transmembrane domain and a cytoplasmic tail. The sequence motif, WQPWS, is present in the membrane-transmembrane proximal cytokine receptor domain, and corresponds to the WSXWS signature motif characteristic of cytokine receptors. See, FIG. 3. The cytoplasmic portion of the human IL-23r comprises 252 amino acids, including seven tyrosine residues. Protein sequence analysis of this cytoplasmic portion reveals three potential Src homology 2 domain-binding sites and two potential Stat-binding sites. These sites display 100% amino acid identity to the mouse and hIL-23R proteins within these motifs. Parham et al., *J. Immunol.* (2002) 168:5699-5708.

The nucleotide and corresponding amino acid sequence for a representative full-length human IL-23r receptor is shown in FIGS. 2A and 2B, respectively (SEQ ID NOS:3 and 4, NCBI Accession No. NM_144701 and NP_055154, respectively). The full-length molecule includes 629 amino acids. Amino acids 1-23 represent a signal peptide. The signal peptide is followed by a 330 amino acid extracellular domain, a 23 amino acid transmembrane domain, and a 253 amino acid cytoplasmic tail. The murine counterpart of hIL-23R is 644 amino acids in length and has 84% sequence homology with the protein-coding regions of the hIL-23R gene. Parham et al., *J. Immunol.* (2002) 168:5699-5708.

As with the IL-17r, the use of a soluble IL-23r is particularly preferred. A soluble IL-23r typically includes the extracellular domain or an active portion thereof but lacks the transmembrane domain and, optionally, the cytoplasmic tail and may or may not include the native or a heterologous signal sequence. One example of a soluble IL-23r comprises the signal peptide and the extracellular domain of the molecule, such as represented by residues 1 to 353 of SEQ ID NO:4, or an active fragment thereof.

Various other IL-17r and IL-23r sequences and variants from humans and other species are known and can also be used herein. If a soluble form of the receptor is desired, the corresponding domains to those described above can be used and are readily identifiable by one of skill in the art, such as by using standard hydropathy plots, such as those calculated using the Kyte-Doolittle technique, Kyte et al., *J. Mol. Biol.* (1982) 157:105-132.

Additional IL-17r sequences and variants thereof for use with the present invention are described in e.g., U.S. Pat. No. 7,256,264, incorporated herein by reference in its entirety, as well as NCBI accession numbers NM_014339, NM_032732, NM_153461, NM_153460, EF676034, NM_018725, AF212365, AF458069, AF458067, EF676033, EF676032, AF458065, U58917 (all human sequences); NM_008359, AK050139, AX720728, AF458066, NM_134159, AF458068, AF208108, U31993 (all mouse sequences); XM_603383 (bovine); XM_001489654 (horse); NM_01107883 (rat); XR_024768 (chimp); XM_533791 (dog).

Non-limiting examples of IL-23r sequences for use with the present invention include the sequences described in NCBI accession numbers Q5VWKS, NM_144701, AF461422 (all human sequences); Q8K4B4, NP653131, NM_144548, AF461423 (all mouse sequences); EU616678 (bovine).

Polynucleotides encoding the desired interleukin receptor for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, *Nature* (1981) 292:756; Nambair et al., *Science* (1984) 22:1299; and Jay et al., *J. Biol. Chem.* (1984) 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., *Proc. Nat. Acad. Sci. USA* (1991) 88:4084-4088. Additionally, oligonucleotide-directed synthesis (Jones et al., *Nature* (1986) 54:75-82), oligonucleotide directed mutagenesis of preexisting nucleotide regions (Riechmann et al., *Nature* (1988) 332:323-327 and Verhoeyen et al., *Science* (1988) 239:1534-1536), and enzymatic filling-in of gapped oligonucleotides using $T_4$ DNA polymerase (Queen et al., *Proc. Nat. Acad. Sci. USA* (1989) 86:10029-10033) can be used to provide molecules for use in the subject methods.

Once obtained, the polynucleotide encoding the interleukin receptor is linked to a multimerization domain either directly or via a linker moiety. A multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in, for example, U.S. Pat. No. 5,731,168, incorporated herein by reference in its entirety. The multimerization domain provides that portion of the molecule which promotes or allows the formation of dimers, trimers, and the like from monomeric domains.

Multimerization domains will cause at least 5%, 10%, 20%, 30%, 40%, 50%, 60%, 75%, 80%, 85%, 90%, or 95% of the monomeric fusion proteins to migrate on a nondenaturing polyacrylamide gel at a rate appropriate for a multimer. Glycosylation can affect the migration of a protein in a gel. Although particular sequences are shown here, variants such as allelic variants can be used as well. Typically such variants will have at least 85%, 90%, 95%, 97%, 98%, or 99% identity with the disclosed sequence.

Multimerization can be assayed, for example, using reducing and non-reducing gels. Multimerization can also be assayed by detection of increased binding affinity of a protein for its ligand/receptor. BiaCore™ surface plasmon resonance assays can be used in this regard. These assays detect changes in mass by measuring changes in refractive index in an aqueous layer close to a sensor chip surface. Any method known in the art can be used to detect multimerization.

Preferably, multimerization domains are derived from immunoglobulin molecules, such as from immunoglobulin constant region domains. Sequences of the Fc portion of IgG1 or IgG2 lambda heavy chain can be used, for example, CH3 alone or portions of CH3, such as amino acids Gly224-Lys330, numbered relative to the human IgG1 Fc portion or both of CH2 and CH3 domains or portions thereof, such as amino acids Pro111-Lys330, numbered relative to the human IgG1 Fc portion.

The Fc portion of an immunoglobulin molecule is obtained by cleavage of whole antibody molecules with the enzyme papain. Other means can be used to obtain these portions. For the IgG1 lambda heavy chain protein sequence, see Genbank accession no Y14737. Other Fc regions can be used for example from other IgG types and from IgA, IgM, IgD, or IgE antibodies.

As explained above, the interleukin receptor can be linked to a multimerization domain via a linker. Linkers are typically polypeptide chains. Linker moieties can include, for example, 3-100 amino acid residues, such as 5-75 amino acid residues, 5-50 amino acid residues, 5-25 amino acid residues, 5-20 amino acid residues, 5-15 amino acid residues, 5-10 amino acid residues, 5-9 amino acid residues, or any number of amino acid residues within these ranges. Examples of useful linkers include: $Gly_9$ (SEQ ID NO:9), $Glu_9$ (SEQ ID NO:10), $Ser_9$ (SEQ ID NO:11), $Gly_5$-Cys-$Pro_2$-Cys (SEQ ID NO:12), $(Gly_4$-Ser$)_3$ (SEQ ID NO:13), Ser-Cys-Val-Pro-Leu-Met-Arg-Cys-Gly-Gly-Cys-Cys-Asn (SEQ ID NO:14), Pro-Ser-Cys-Val-Pro-Leu-Met-Arg-Cys-Gly-Gly-Cys-Cys-Asn (SEQ ID NO: 15), Gly-Asp-Leu-Ile-Tyr-Arg-Asn-Gln-Lys (SEQ ID NO:16), and $Gly_9$-Pro-Ser-Cys-Val-Pro-Leu-Met-Arg-Cys-Gly-Gly-Cys-Cys-Asn (SEQ ID NO:17). Other polypeptide linkers which can be used include a polyglycine of different lengths, including for example, 5, 7, or 30 residues. Additionally, portions of Flt-1 can be used as a linker, for example domain 3 of Flt-1.

Linker moieties can also be made from other polymers, such as polyethylene glycol. Such linkers can have from 10-1000, 10-500, 10-250, 10-100, or 10-50 ethylene glycol monomer units, or any number of monomer units within these ranges. Suitable polymers should be of a size similar to the size occupied by the appropriate range of amino acid residues. A typical sized polymer provides a spacing of from about 10-25 angstroms.

The sequences for the multimerization domain and the linker moiety can be obtained as described above with respect to the interleukin receptor.

Figure 4:
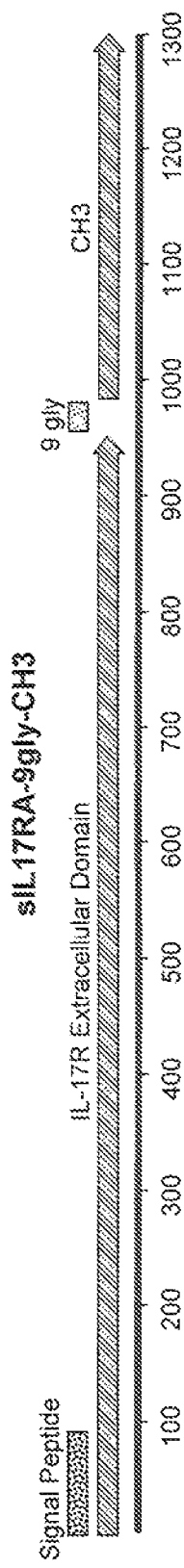
FIG. 4 is a diagrammatic representation of a fusion construct including a soluble IL-17rA linked to the CH3 domain of the Fc region of a human IgG1 immunoglobulin via a linker of nine Gly residues (sIL17R-9gly-CH3).

Particularly preferred fusions include those depicted diagrammatically in FIGS. 3 and 4, the sequences of which are presented in FIGS. 5A-5B (SEQ ID NOS:5 and 6) and FIGS. 6A-6B (SEQ ID NOS:7 and 8), respectively. As shown in FIG. 3, the construct encodes a soluble human IL-23r, linked by a sequence of nine glycines to the CH3 domain of the human IgG1 Fc domain. As shown in FIG. 4, the construct encodes a soluble human IL-17r linked by a sequence of nine glycines to the CH3 domain of the human IgG1 Fc domain.

Once produced, the constructs are delivered using recombinant viral vectors as described further below.

Gene Delivery Techniques

The constructs described above, are delivered to the subject in question using any of several gene-delivery techniques. Several methods for gene delivery are known in the art. As described further below, genes can be delivered either directly to the subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described. See, e.g., U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Replication-defective murine retroviral vectors are widely utilized gene transfer vectors. Murine leukemia retroviruses include a single strand RNA complexed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476). Adenovirus vectors for use in the subject methods are described in more detail below.

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875. AAV vector systems are also described in further detail below.

Additional viral vectors which will find use for delivering the nucleic acid molecules of interest include those derived from the pox family of viruses, including vaccinia virus and avian poxvirus. By way of example, vaccinia virus recombinants expressing the genes can be constructed as follows. The DNA encoding the particular polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the protein into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Nat. Acad. Sci. USA* (1992) 89:6099-6103, can also be used for gene delivery.

Members of the Alphavirus genus, such as but not limited to vectors derived from the Sindbis and Semliki Forest viruses, will also find use as viral vectors for delivering the polynucleotide encoding the fusion. For a description of Sinbus-virus derived vectors useful for the practice of the instant methods, see, Dubensky et al., *J. Virol.* (1996) 70:508-519; and International Publication Nos. WO 95/07995 and WO 96/17072.

Alternatively, the interleukin receptor fusions can be delivered without the use of viral vectors, such as by using plasmid-based nucleic acid delivery systems as described in U.S. Pat. Nos. 6,413,942; 6,214,804; 5,580,859; 5,589,466; 5,763,270; and 5,693,622, all incorporated herein by reference in their entireties. Plasmids will include the gene of interest operably linked to control elements that direct the expression of the protein product in vivo. Such control elements are well known in the art.

Adenovirus Gene Delivery Systems

In one embodiment of the subject invention, a nucleotide sequence encoding the fusions is inserted into an adenovirus-based expression vector. The adenovirus genome is a linear double-stranded DNA molecule of approximately 36,000 base pairs with the 55-kDa terminal protein covalently bound to the 5' terminus of each strand. Adenoviral ("Ad") DNA contains identical Inverted Terminal Repeats ("ITRs") of about 100 base pairs with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single-stranded and can form a "panhandle" intermediate, which allows replication initiation and generation of a daughter duplex molecule. Alternatively, replication can proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins. During the late phase, late viral gene products are expressed in addition to the early gene products and host cell DNA and protein synthesis are shut off. Consequently, the cell becomes dedicated to the production of viral DNA and of viral structural proteins.

The E1 region of adenovirus is the first region expressed after infection of the target cell. This region consists of two transcriptional units, the E1A and E1B genes. The main functions of the E1A gene products are to induce quiescent cells to enter the cell cycle and resume cellular DNA synthesis, and to transcriptionally activate the E1B gene and the other early regions (E2, E3, E4). Transfection of primary cells with the E1A gene alone can induce unlimited proliferation (immortalization), but does not result in complete transformation. However, expression of E1A in most cases results in induction of programmed cell death (apoptosis), and only occasionally immortalization. Coexpression of the E1B gene is required to prevent induction of apoptosis and for complete morphological transformation to occur. In established immortal cell lines, high level expression of EA can cause complete transformation in the absence of E1B.

The E1B-encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomittantly with the onset of the late phase of infection. The E1B 21 kD protein is important for correct temporal control of the productive infection cycle, thereby preventing premature death of the host cell before the virus life cycle has been completed.

Adenoviral-based vectors express gene product peptides at high levels. Adenoviral vectors have high efficiencies of infectivity, even with low titers of virus. Additionally, the virus is fully infective as a cell-free virion so injection of producer cell lines are not necessary. Adenoviral vectors achieve long-term expression of heterologous genes in vivo. Adenovirus is not associated with severe human pathology, the virus can infect a wide variety of cells and has a broad host-range, the virus can be produced in large quantities with relative ease, and the virus can be rendered replication defective by deletions in the early-region 1 ("E1") of the viral genome. Thus, vectors derived from human adenoviruses, in which at least the E1 region has been deleted and replaced by a gene of interest, have been used extensively for gene therapy experiments in the pre-clinical and clinical phase.

Adenoviral vectors for use with the present invention are derived from any of the various adenoviral serotypes, including, without limitation, any of the over 40 serotype strains of adenovirus, such as serotypes 2, 5, 12, 40, and 41. The adenoviral vectors used herein are replication-deficient and contain the gene of interest under the control of a suitable promoter, such as any of the promoters discussed below with reference to adeno-associated virus. For example, U.S. Pat. No. 6,048,551, incorporated herein by reference in its entirety, describes replication-deficient adenoviral vectors that include the human gene for the anti-inflammatory cytokine IL-10, as well as vectors that include the gene for the anti-inflammatory cytokine IL-1ra, under the control of the Rous Sarcoma Virus (RSV) promoter, termed Ad.RSVIL-10 and Ad.RSVIL-1ra, respectively.

Other recombinant adenoviruses, derived from any of the adenoviral serotypes, and with different promoter systems, can be used by those skilled in the art. For example, U.S. Pat. No. 6,306,652, incorporated herein by reference in its entirety, describes adenovirus vectors with E2A sequences, containing the hr mutation and the ts125 mutation, termed ts400, to prevent cell death by E2A overexpression, as well as vectors with E2A sequences, containing only the hr mutation, under the control of an inducible promoter, and vectors with E2A sequences, containing the hr mutation and the ts125 mutation (ts400), under the control of an inducible promoter.

Moreover, "minimal" adenovirus vectors as described in U.S. Pat. No. 6,306,652 will find use with the present invention. Such vectors retain at least a portion of the viral genome that is required for encapsidation of the genome into virus particles (the encapsidation signal), as well as at least one copy of at least a functional part or a derivative of the ITR. Packaging of the minimal adenovirus vector can be achieved by co-infection with a helper virus or, alternatively, with a packaging-deficient replicating helper system as described in U.S. Pat. No. 6,306,652.

Other useful adenovirus-based vectors for delivery of the gene of interest include the "gutless" (helper-dependent) adenovirus in which the vast majority of the viral genome has been removed (Wu et al., *Anesthes*. (2001) 94:1119-1132). Such "gutless" adenoviral vectors essentially create no viral proteins, thus allowing virally driven gene therapy to successfully ensue for over a year after a single administration (Parks, R. J., *Clin. Genet*. (2000) 58:1-11; Tsai et al., *Curr. Opin. Mol. Ther*. (2000) 2:515-523) and eliminates interference by the immune system. In addition, removal of the viral genome creates space for insertion of control sequences that provide expression regulation by systemically administered drugs (Burcin et al., *Proc. Natl. Acad. Sci. USA* (1999) 96:355-360), adding both safety and control of virally driven protein expression. These and other recombinant adenoviruses will find use with the present methods.

Adeno-Associated Virus Gene Delivery Systems

Adeno-associated virus (AAV) has been used with success to deliver genes for gene therapy. The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene (in this case, the gene encoding the interleukin receptor fusion) between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

AAV is a helper-dependent virus; that is, it requires coinfection with a helper virus (e.g., adenovirus, herpesvirus or vaccinia), in order to form AAV virions. In the absence of coinfection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

Recombinant AAV virions comprising the gene of interest may be produced using a variety of art-recognized techniques described more fully below. Wild-type AAV and helper viruses may be used to provide the necessary replicative functions for producing rAAV virions (see, e.g., U.S. Pat. No. 5,139,941, incorporated herein by reference in its entirety). Alternatively, a plasmid, containing helper function genes, in combination with infection by one of the well-known helper viruses can be used as the source of replicative functions (see e.g., U.S. Pat. Nos. 5,622,856 and 5,139,941, both incorporated herein by reference in their entireties). Similarly, a plasmid, containing accessory function genes can be used in combination with infection by wild-type AAV, to provide the necessary replicative functions. These three approaches, when used in combination with a rAAV vector, are each sufficient to produce rAAV virions. Other approaches, well known in the art, can also be employed by the skilled artisan to produce rAAV virions.

In one embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. Preferably, the AAV helper function vector supports efficient AAV vector production without generating any detectable wt AAV virions (i.e., AAV virions containing functional rep and cap genes). An example of such a vector, pHLP19, is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV-derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In a preferred embodiment, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

In order to further an understanding of AAV, a more detailed discussion is provided below regarding recombinant AAV expression vectors and AAV helper and accessory functions Recombinant AAV Expression Vectors Recombinant AAV (rAAV) expression vectors are constructed using known techniques to at least provide as operatively linked components in the direction of transcription, control elements including a transcriptional initiation region, the polynucleotide of interest and a transcriptional termination region. The control elements are selected to be functional in the cell of interest, such as in a mammalian cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable polynucleotide molecules for use in AAV vectors will be less than about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV expression vector which harbors the polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.*

158:97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

For the purposes of the invention, suitable host cells for producing rAAV virions from the AAV expression vectors include microorganisms, yeast cells, insect cells, and mammalian cells, that can be, or have been, used as recipients of a heterologous DNA molecule and that are capable of growth in, for example, suspension culture, a bioreactor, or the like. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241-247; McPherson et al. (1985) *Virology* 147:217-222; Schlehofer et al. (1986) *Virology* 15:110-117.

Alternatively, accessory functions can be provided using an accessory function vector as defined above. See, e.g., U.S. Pat. No. 6,004,797 and International Publication No. WO 01/83797, incorporated herein by reference in their entireties. Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 12:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions, in I CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, has reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions. A "recombinant AAV virion," or "rAAV virion" is defined herein as an infectious, replication-defective virus including an AAV protein shell, encapsidating a heterologous nucleotide sequence of interest which is flanked on both sides by AAV ITRs.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the nucleotide sequence of interest can then be used for gene delivery using the techniques described below.

Compositions and Delivery

A. Compositions

Once produced, the vectors (or virions) encoding the fusions, will be formulated into compositions suitable for delivery. Compositions will comprise sufficient genetic material to produce a therapeutically effective amount of the interleukin receptor of interest, i.e., an amount sufficient to bind to and mediate the effects of the corresponding signal pathway. The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

One particularly useful formulation comprises the vector or virion of interest in combination with one or more dihydric or polyhydric alcohols, and, optionally, a detergent, such as a sorbitan ester. See, for example, U.S. Pat. No. 6,764,845, incorporated herein by reference in its entirety.

As is apparent to those skilled in the art in view of the teachings of this specification, an effective amount can be empirically determined. Representative doses are detailed below. Administration can be effected in one dose, continuously or intermittently throughout the course of treatment. Methods of determining the most effective means and dosages of administration are well known to those of skill in the art and will vary with the vector, the composition of the therapy, the target cells, and the subject being treated. Single and multiple administrations can be carried out with the dose level and pattern being selected by the treating physician.

If multiple doses are administered, the first formulation administered can be the same or different than the subsequent formulations. Thus, for example, the first administration can be in the form of an adenovirus vector and the second administration in the form of an adenovirus vector, plasmid DNA, an AAV virion, a subunit vaccine composition, or the like. Moreover, subsequent delivery can also be the same or different than the second mode of delivery.

It should be understood that more than one transgene can be expressed by the delivered recombinant vector. Alternatively, separate vectors, each expressing one or more different transgenes, can also be delivered to the subject as described herein. Thus, multiple transgenes can be delivered concurrently or sequentially. Furthermore, it is also intended that the vectors delivered by the methods of the present invention be combined with other suitable compositions and therapies. For instance, other immune modulators can be present.

Fusion proteins according to the invention can be made by any means known in the art. While such proteins can be made synthetically, or by linking portions which are made, recombinant production can also be used. A fused gene sequence can be produced using the standard tools of recombinant DNA. The fused gene sequence can be inserted into a vector, for example a viral or plasmid vector, for replicating the fused gene sequence. A promoter sequence which is functional in the ultimate recipient cell can be introduced upstream of the fused gene sequence. Promoters used can be constitutive, inducible or repressible. Examples of each type are well-known in the art. The vector can be introduced into a host cell or mammal by any means known in the art. Suitable vectors which can be used include adenovirus, adeno-associated virus, retrovirus, lentivirus, and plasmids. If the vector is in a viral vector and the vector has been packaged, then the virions can be used to infect cells. If naked DNA is used, then transfection or transformation procedures as are appropriate for the particular host cells can be used. Formulations of naked DNA utilizing polymers, liposomes, or nanospheres can be used for fusion gene delivery.

Cells which can be transformed or transfected with recombinant constructs according to the invention may be any which are convenient to the artisan. Exemplary cell types which may be used include bacteria, yeast, insects, and mammalian cells. Among mammalian cells, cells of many tissue types may be chosen, as is convenient. Exemplary cells which may be used are fibroblasts, hepatocytes, endothelial cells, stem cells, hematopoietic cells, epithelial cells, myocytes, neuronal cells, and keratinocytes. These cells can be used to produce protein in vitro, or can be delivered to mammals including humans to produce the encoded proteins in vivo. This means of delivery is an alternative to delivering nucleic acid to a mammal, delivering viral vector to a mammal, and delivering fusion protein to a mammal.

Compositions of protein or nucleic acids can be in carriers, such as buffers, aqueous or lipophilic carriers, sterile or non-sterile, pyrogenic or non-pyrogenic vehicles. Non-pyrogenic vehicles are useful for injectible formulations. Formulations can be liquid or solid, for example, lyophilized. Formulations can also be administered as aerosols. Compositions may contain one or more fusion proteins or one or more nucleic acids, or both fusion proteins and nucleic acids. The fusion proteins and or nucleic acids in a composition may be homogeneous, in which case homomultimer proteins will form, or they may be heterogeneous in the composition, in which case heteromultimer proteins will form.

B. Delivery

Generally, the recombinant vectors are introduced into the subject using either in vivo or in vitro transduction techniques. If transduced in vitro, the desired recipient cell will be removed from the subject, transduced with the recombinant vector and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant vectors with the subject's cells e.g., in appropriate media, and screening for those cells harboring the DNA of interest using conventional techniques such as Southern blots and/or PCR, or by using selectable markers.

The recombinant vectors or transduced cells can be formulated into pharmaceutical compositions, described above, and the composition introduced into the subject by various techniques, such as but not limited to topical, dermal, transdermal, transmucosal, epidermal, parenteral, gastrointestinal, and naso-pharyngeal and pulmonary, including transbronchial and transalveolar administration. Parenteral administration includes intramuscular, intravenous, intraarterial, subcutaneous and intraperitoneal injection, or by injection directly into smooth and cardiac muscle, using e.g., a catheter. Delivery can also be directly into a target organ or desired target tissue.

Pharmaceutical compositions will comprise sufficient genetic material to produce a therapeutically effective amount of the protein of interest, i.e., an amount sufficient to bind to and/or modulate the IL-23 or IL-17 pathways, or to reduce or ameliorate symptoms of the disease state in question, or an amount sufficient to confer the desired benefit. Appropriate doses will also depend on the mammal being treated (e.g., human or nonhuman primate or other mammal), age and general condition of the subject to be treated, the severity of the condition being treated, the mode of administration, among other factors. An appropriate effective amount can be readily determined by one of skill in the art.

Fusion proteins can be provided to a cell or mammalian host by any means known in the art. Protein can be delivered to the cell or host. Nucleic acid can be administered to the cell or host. Transformed or transfected cells can be administered to the cell or host. In the latter case, cells of the same genetic background are desired to reduce transplantation rejection.

Suitable cells for delivery to mammalian host animals include any mammalian cell type from any organ, tumor, or cell line. For example, human, murine, goat, ovine, bovine, dog, cat, and porcine cells can be used. Suitable cell types for use include without limitation, fibroblasts, hepatocytes, endothelial cells, keratinocytes, hematopoietic cells, epithelial cells, myocytes, neuronal cells, and stem cells.

Means of delivery of fusion proteins or nucleic acids encoding fusion proteins include delivery of cells expressing the fusion proteins, delivery of the fusion proteins, and delivery of nucleic acids encoding the fusion proteins. Fusion proteins, cells, or nucleic acids can be delivered directly to the desired organ or tumor, for example by injection, catheterization, or endoscopy. They can also be delivered intravenously, intrabronchially, intra-tumorally, intrathecally, intramuscularly, intraocularly, topically, subcutaneously, transdermally or per os.

Combinations of protein and nucleic acid treatments can be used. For example, a fusion protein according to the invention can be administered to a patient. If a favorable response is observed, then a nucleic acid molecule encoding the fusion protein can be administered for a long term effect. Alternatively, the protein and nucleic acid can be administered simultaneously or approximately simultaneously.

Thus, a "therapeutically effective amount" will fall in a relatively broad range that can be determined through clinical trials. For example, for in vivo injection of rAAV virions, a therapeutically effective dose will be on the order of from about $10^6$ to $10^{15}$ of the recombinant virus, more preferably $10^8$ to $10^{14}$ recombinant virus. For adenovirus-delivered fusions, a therapeutically effective dose will include about $1 \times 10^6$ plaque forming units (PFU) to $1 \times 10^{12}$ PFU, preferably about $1 \times 10^7$ PFU to about $1 \times 10^{10}$ PFU, or any dose within these ranges which is sufficient to provide the desired affect.

For in vitro transduction, an effective amount of rAAV virions to be delivered to cells will be on the order of $10^8$ to $10^{13}$ of the recombinant virus. The amount of transduced cells in the pharmaceutical compositions will be from about $10^4$ to $10^{10}$ cells, more preferably $10^5$ to $10^8$ cells. Other effective dosages can be readily established by one of ordinary skill in the art through routine trials establishing dose response curves.

Generally, from 1 µl to 1 ml of composition will be delivered, such as from 0.01 to about 0.5 ml, for example about 0.05 to about 0.3 ml, such as 0.08, 0.09, 0.1, 0.2, etc. and any number within these ranges, of composition will be delivered.

For protein administration, dosage amounts may vary from about 10 ng/kg to up to 100 mg/kg of body weight or more per day, preferably about 1 µg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212.

Dosage treatment may be a single dose schedule or a multiple dose schedule. Moreover, the subject may be administered as many doses as appropriate. One of skill in the art can readily determine an appropriate number of doses.

Immune-Related and Inflammatory Disorders

As explained above, the fusions of the invention can be used to bind to and mediate the IL-17 and IL-23 signal pathways, and are therefore useful in the treatment of a wide variety of immune-related disorders and inflammatory diseases. Examples of such disorders, some of which are immune or T-cell mediated, include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease, infectious diseases including viral diseases such as AIDS (HIV infection), hepatitis A, B, C, D, and E, herpes, etc., bacterial infections, fungal infections, protozoal infections and parasitic infections, and cancer.

In certain embodiments, an individual at risk of developing an immune-related disorder or inflammatory disease is administered an amount effective to delay or prevent the disease. Individuals at risk of developing an immune-related disease, such as an autoimmune disease include, for example, those with a genetic or other predisposition toward developing such disease. In humans, susceptibility to particular autoimmune diseases is associated with HLA type with some being linked most strongly with particular MHC class II alleles and others with particular MHC class I alleles. For example, ankylosing spondylitis, acute anterior uveitis, and juvenile rheumatoid arthritis are associated with HLA-B27, Goodpasture's syndrome and MS are associated with HLA-DR2, Grave's disease, myasthenia gravis and SLE are associated with HLA-DR3, rheumatoid arthritis and pemphigus vulgaris are associated with HLA-DR4 and Hashimoto's thyroiditis is associated with HLA-DR5. Other genetic predispositions to autoimmune diseases are known in the art and an individual can be examined for existence of such predispositions by assays and methods well known in the art. Accordingly, in some instances, an individual at risk of developing an immune-related disorder can be identified.

Animal models for the study of immune-related diseases are known in the art.

For example, animal models which appear most similar to human disease include animal strains which spontaneously develop a high incidence of the particular disease. Examples of such models include, but are not limited to, the nonobese diabetic (NOD) mouse, which develops a disease similar to type 1 diabetes, and lupus-like disease prone animals, such as New Zealand hybrid, MRL-Fas$^{lpr}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-receptor antagonist knockout for rheumatoid arthritis.

Accordingly, animal models standard in the art are available for the screening and/or assessment for activity and/or effectiveness of the methods and compositions of the invention for the treatment of immune-related disorders.

Kits of the Invention

The invention also provides kits. In certain embodiments, the kits of the invention comprise one or more containers comprising purified an interleukin receptor-immunoglobulin fusion and/or recombinant vectors encoding such a fusion. The kits may further comprise a suitable set of instructions, generally written instructions, relating to the use of the proteins and vectors for any of the methods described herein, such as modulating IL-17 or IL-23 activity, ameliorating one or more symptoms of an immune-related disease, ameliorating a symptom of chronic inflammatory disease, decreasing an immune response to a virus, and the like.

The kits may comprise the components in any convenient, appropriate packaging. For example, if the fusion proteins or recombinant vectors are provided as a dry formulation (e.g., freeze dried or a dry powder), a vial with a resilient stopper is normally used, so that the vectors may be easily resuspended by injecting fluid through the resilient stopper. Ampules with non-resilient, removable closures (e.g., sealed glass) or resilient stoppers are most conveniently used for liquid formulations. Also contemplated are packages for use in combination with a specific device, such as an inhaler, nasal administration device (e.g., an atomizer), a syringe or an infusion device such as a minipump.

The instructions relating to the use or the recombinant vectors generally include information as to dosage, dosing schedule, and route of administration for the intended method of use. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

2. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Construction of Soluble IL-17 and IL-23 Receptors

Figure 7:
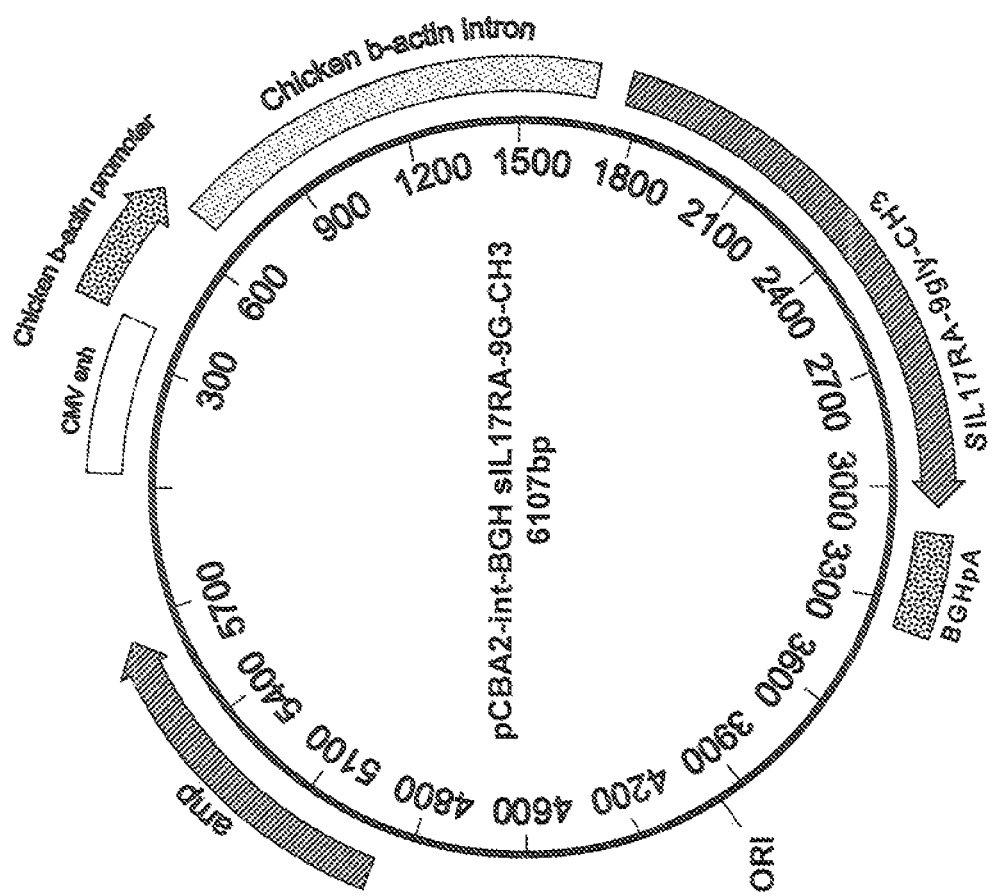
FIG. 7 is a diagram of plasmid pCBA2-int-BGH sIL17R-9G-CH3.
Figure 8:
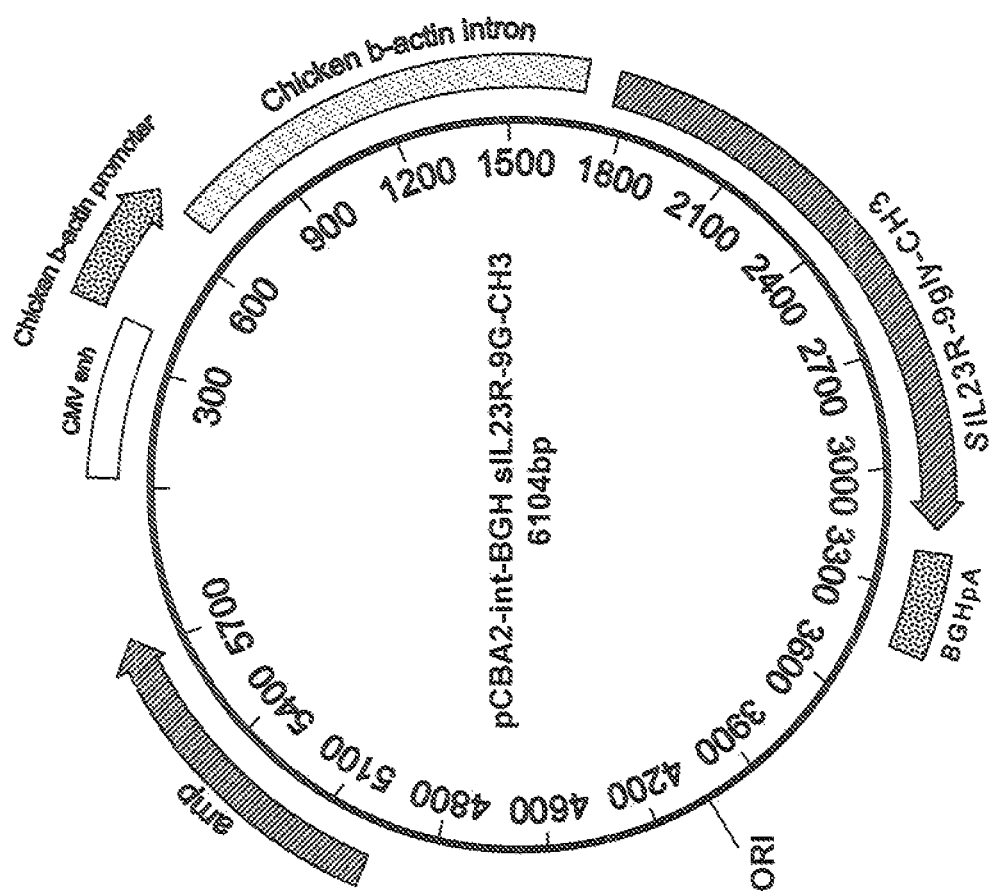
FIG. 8 is a diagram of plasmid pCBA2-int-BGH sIL23R-9G-CH3.

Soluble receptors containing the extracellular domains of the human IL-17 and IL-23 receptors were cloned in-frame to a 9-Gly linker followed by the CH3 region of human IgG1 driven using the chicken β-actin promoter and CMV enhancer. Plasmid pCBA2-int-BGH sIL17R-9G-CH3 is depicted in FIG. 7; and plasmid pCBA2-int-BGH sIL23R-9G-CH3 is depicted in FIG. 8.

The final IL-23r and IL-17r fusions are shown in FIGS. 3 and 4, respectively, and the sequences are presented in FIGS. 5A-5B (SEQ ID NOS:5 and 6) and FIGS. 6A-6B (SEQ ID NOS:7 and 8), respectively. As shown in FIG. 3, the IL-23r construct encodes a soluble IL-23r, including amino acids 1 to 347 of human IL-23r, linked by a sequence of nine glycines to the CH3 domain, amino acids 225 to 330 of the human IgG1 C region. As shown in FIG. 6B (SEQ ID NO:8), the IL-17r construct encodes a soluble IL-17r, including amino acids 1 to 317 of human IL-17r, followed by a substitution of threonine at position 318 for proline present in human IL-17r, linked by a sequence of nine glycines to the CH3 domain, amino acids 225 to 330 of the human IgG1 C region. The constructs were incorporated into adenovirus and rAAV virions as follows.

The hIL-17R-9gly-CH3 chimera was constructed from a PCR fragment consisting of the signal peptide and extracellular domain (EC) (aa 1-317) of human IL-17RA, followed by a substitution of threonine at position 318 for proline present in human IL-17RA. The EC domain fragment was linked in-frame to a 9-gly amino acid linker, followed by the human IgG1 CH3 region.

The hIL-23R-9gly-CH3 chimera was similarly constructed from a PCR fragment consisting of the EC (aa 1-347) of the hIL-23r subunit plus 9-gly and human IgG1 CH3 region. Note that this chimera is a homodimer of the hIL-23r subunit. This differs from the native IL-23 receptor, which is a heterodimer of the hIL-23r subunit and the hIL-12rβ1 subunit.

Expression for both chimers was driven from the chicken β-actin (CBA) promoter.

Recombinant AAV virions were produced essentially as described in Pechan et al., "Novel anti-VEGF Chimeric Molecules Delivered by AAV vectors for Inhibition of Retinal Neovascularization" *Gene Ther.* Jul. 17, 2008 (Epub). For all viral constructs, the CBA expression cassettes were inserted into AAV pre-viral plasmids containing stuffer DNA flanked by AAV-2 inverted terminal repeats.

Viruses were produced by triple-transfection of previral plasmid, helper plasmid, and AAV rep/cap plasmid in 293 cells. Resulting AAV particles were purified by iodixanol gradient and Q column. DNase-resistant particle concentration was determined by quantitative PCR.

For recombinant adenovirus vectors, expression cassettes from pCBA2/IL-17R/9gly/CH3 and pCBA2/IL-23R/9gly/CH3 were cloned into pre-adenovirus plasmids and adenovirus lysates were generated in 293 cells as described by Souza and Armentano, *Biotechniques* (1999) 26:502-508. All vectors were propagated in 293 cells and purified by CsCl centrifugation as previously described by Rich et al., *Hum. Gene Ther.* (1993) 4:461-476.

Protein expression was verified by Western analysis and ELISA.

Example 2

Ligand Binding Capabilities of Soluble IL-17 and IL-23 Receptors

Ligand Binding Assays: Conditioned media containing soluble ligands were generated in transfected or virally-infected 293 cells. Receptor concentrations in collected media were determined by ELISA and Western blot. Ligand binding assays were performed on immunoassay plates coated with target ligand rhIL-17 or rhIL-23. Typically conditioned media containing serial dilutions of soluble receptor were incubated with immobilized ligand 1-2 hours at room temperature. Unbound ligand was washed away and bound protein was detected and quantified with receptor-specific detection antibodies, as is performed in an ELISA.

In order to test the ability of the soluble IL-17 and IL-23 receptor fusions to bind to their respective ligands, the following experiments were conducted. In one experiment, the ability of the soluble receptors to bind immobilized ligands was explored. Conditioned media for each receptor was generated from Ad-infected A459 cells and quantified by ELISA as described. Binding was measured on ELISA plates pre-coated with IL-23 or IL-17 ligand. Relative binding was compared to purchased receptor/Fc chimeras (R&D Systems, Minneapolis, Minn.). The control IL-17R/Fc from R&D contains human IL-17R(Met1-Trp320) fused to IEGRMD and human IgG1(Pro100-Lys330). The control IL-23R/Fc from R&D contains human CD33 signal peptide (Met1-Ala16)-humanIL-23R(Gly24-Asp323) fused to IEGRMD and human IgG1(Pro100-Lys330).

Figure 9A:
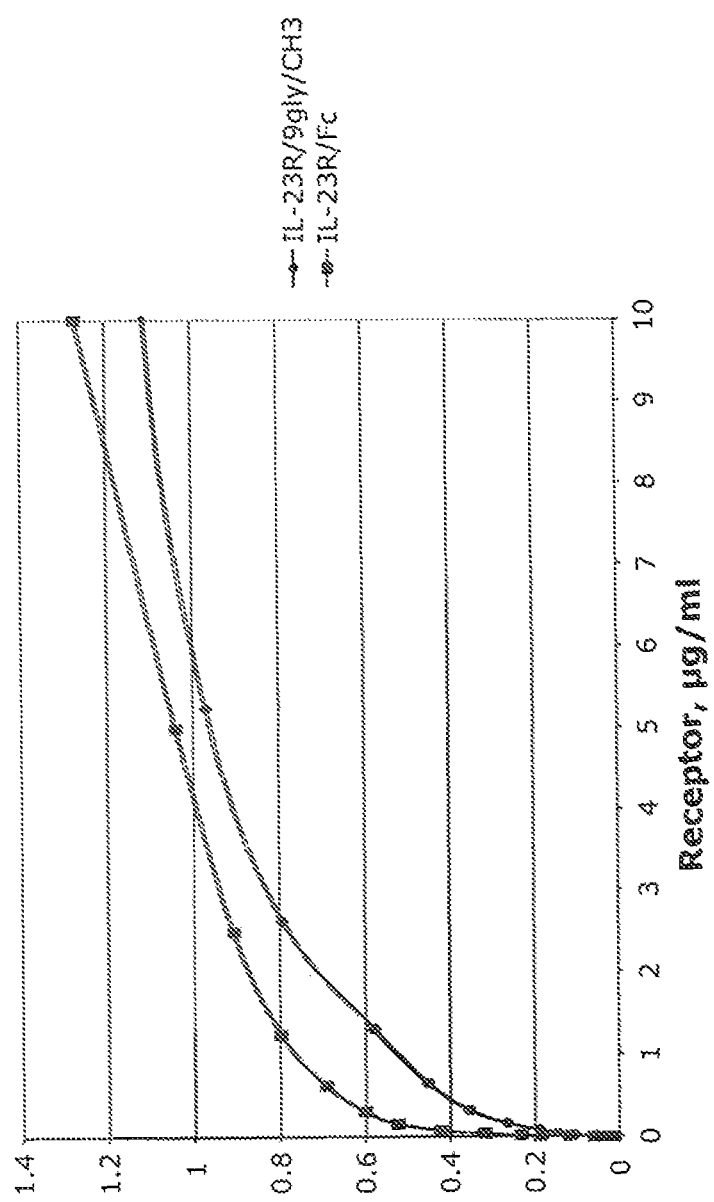
FIGS. 9A and 9B show soluble IL-23r and soluble IL-17r binding to immobilized IL-23 (FIG. 9A) and IL-17 (FIG. 9B), respectively.
Figure 9B:
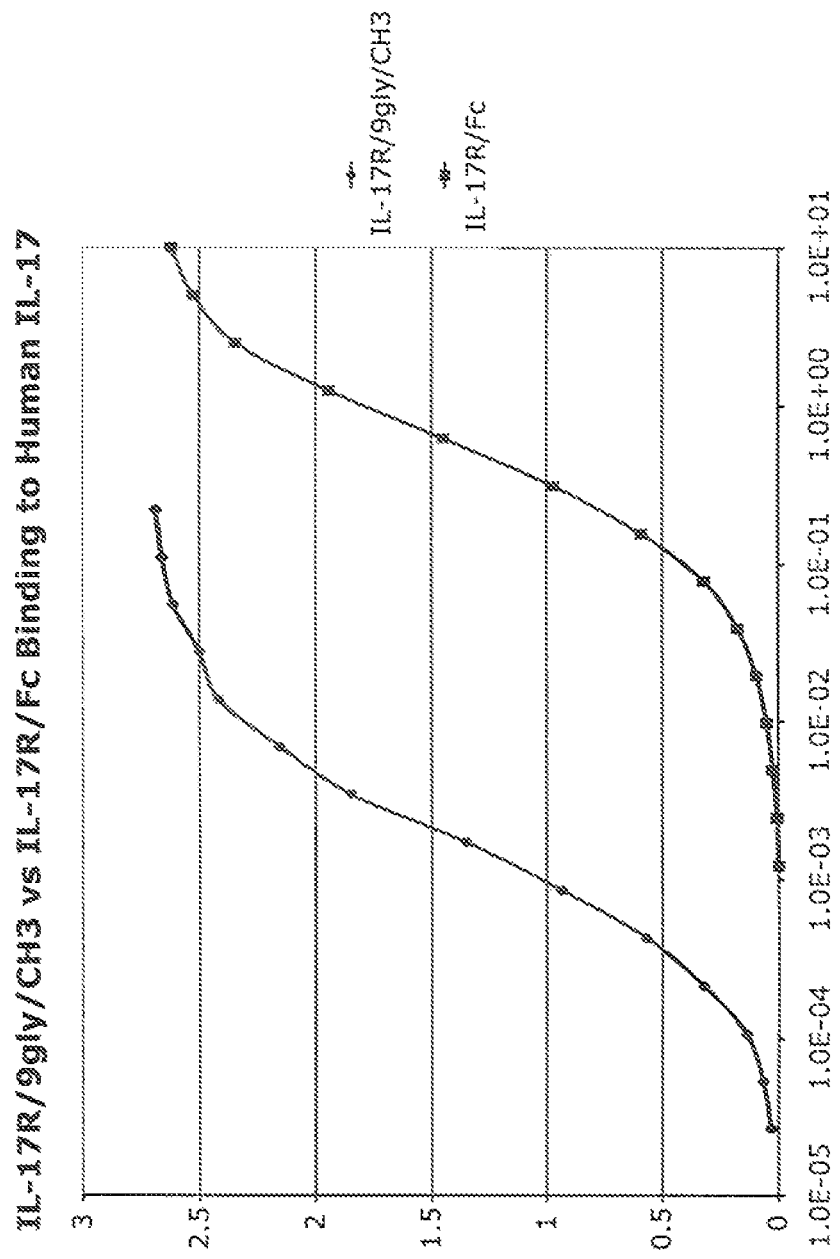

Results are shown in FIGS. 9A and 9B. As can be seen, both receptors bound their respective ligands.

Next, the soluble IL-17r construct described above was tested for its ability to bind to free IL-17 in solution using a competition ELISA. IL-17 at 1 ng/ml was preincubated with serial dilutions of the IL-17r/9gly/CH3 construct, or IL-23r/Fc. Free IL-17 was measured by ELISA after incubation for one hour at room temperature.

Figure 10:
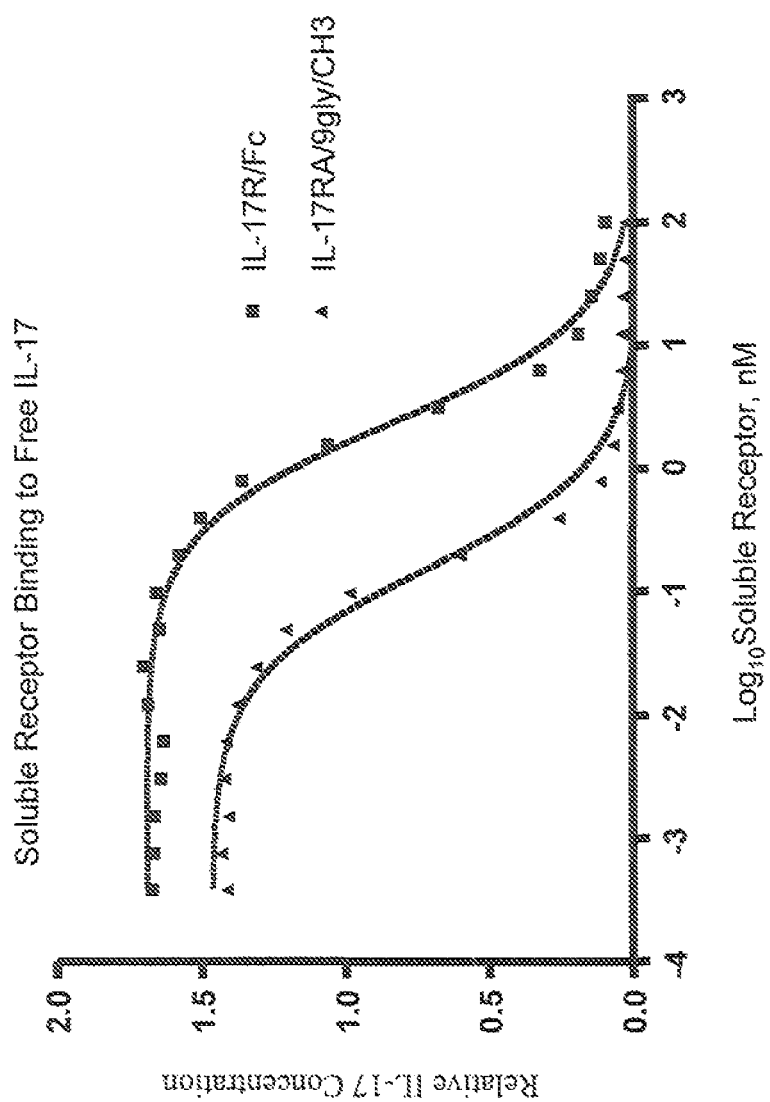
FIG. 10 shows the results of a competition ELISA for soluble IL-17r binding to free IL-17 in solution.
Figure 11:
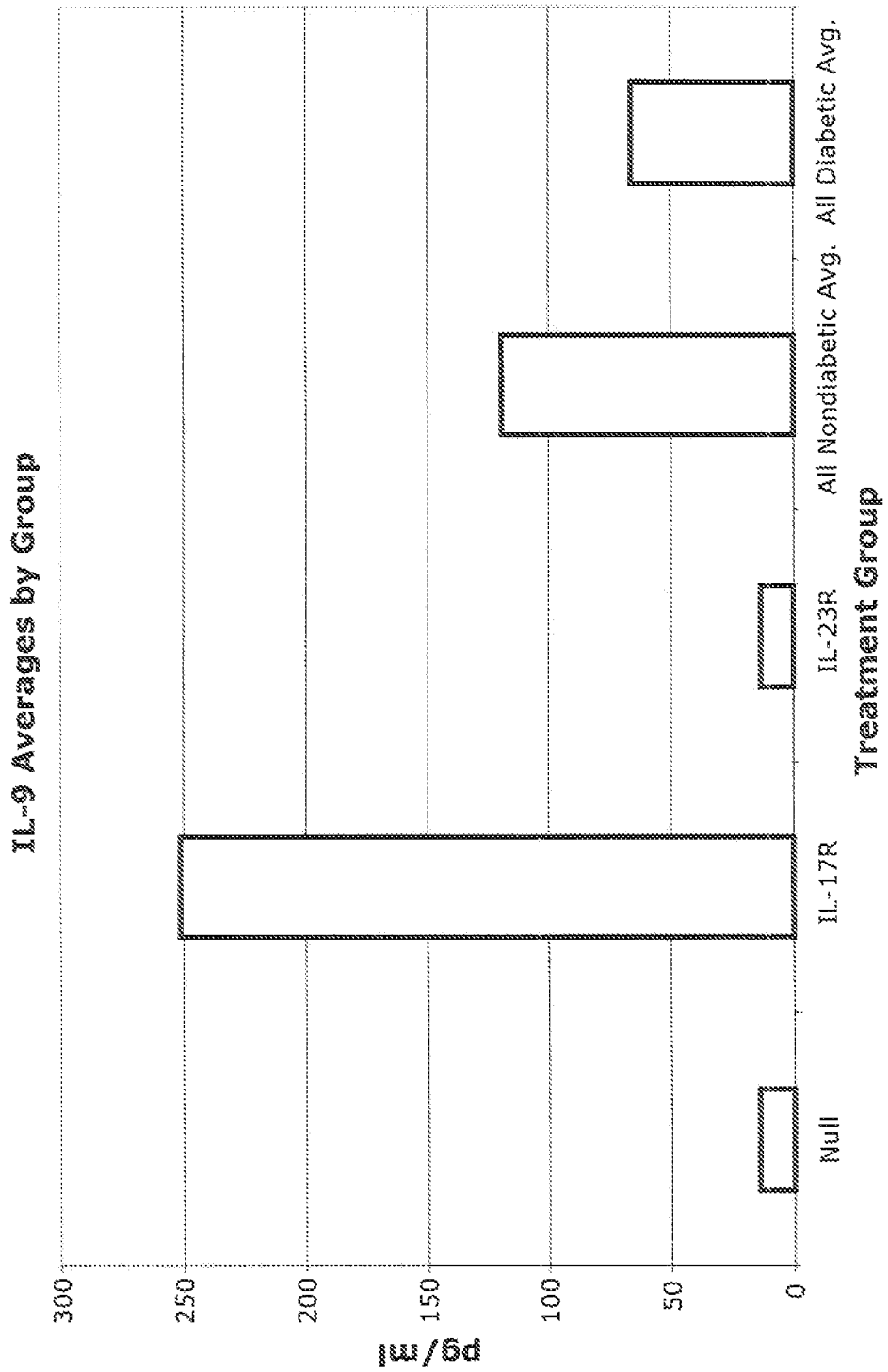
FIG. 11 shows AAV1/IL-17R/9gly/CH3 injection leads to an increase in IL-9 levels relative to AAV1/null and AAV1/IL-23R/9gly/CH3. By comparison, an average non-diabetic NOD mouse had higher IL-9 levels than an average diabetic NOD mouse.
Figure 12:
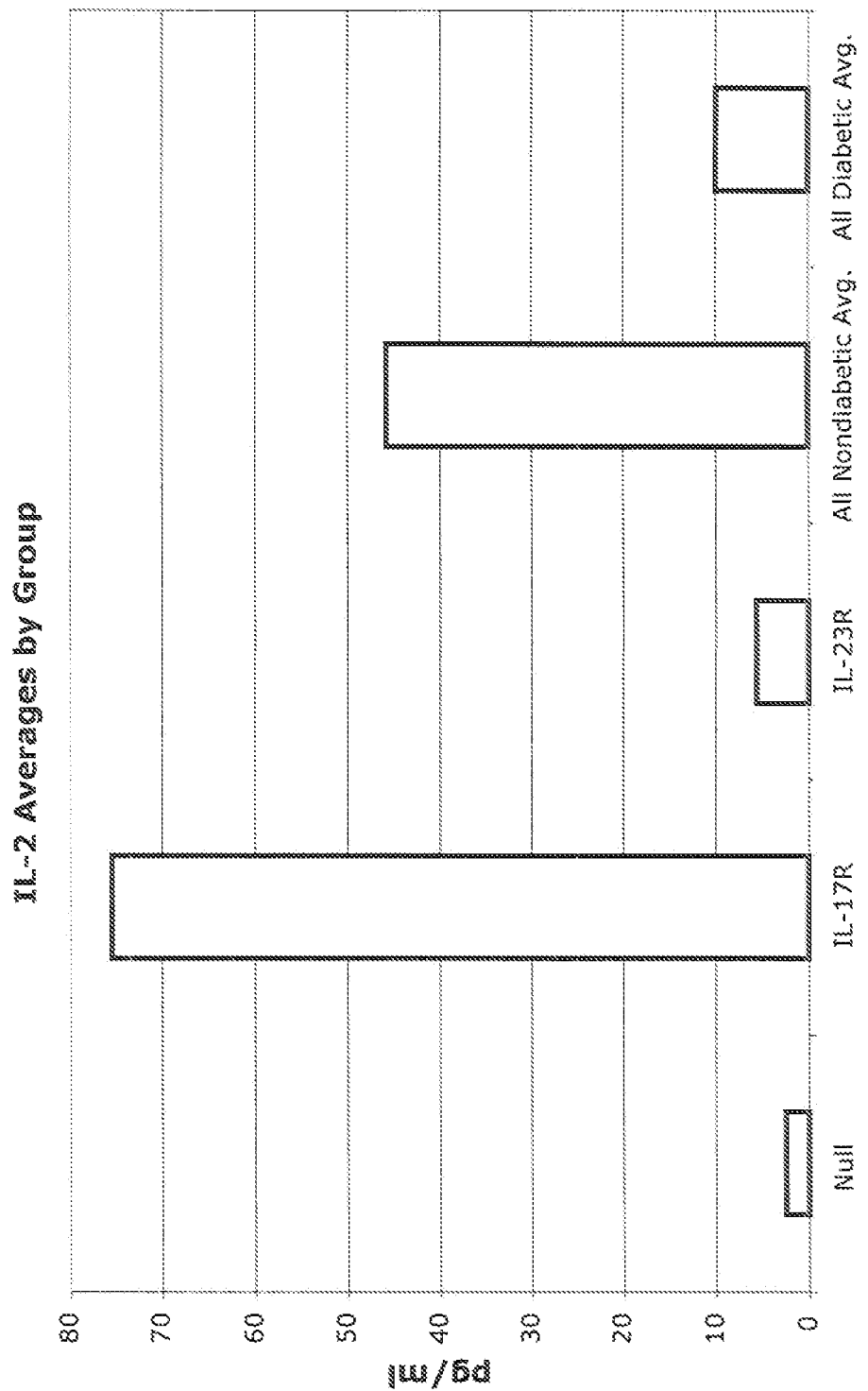
FIG. 12 shows AAV1/IL-17R/9gly/CH3 injection leads to an increase in IL-2 levels relative to AAV1/null and AAV1/IL-23R/9gly/CH3. By comparison, non-diabetic NOD mice in this study had higher IL-2 levels than the diabetic NOD mice.
Figure 13:
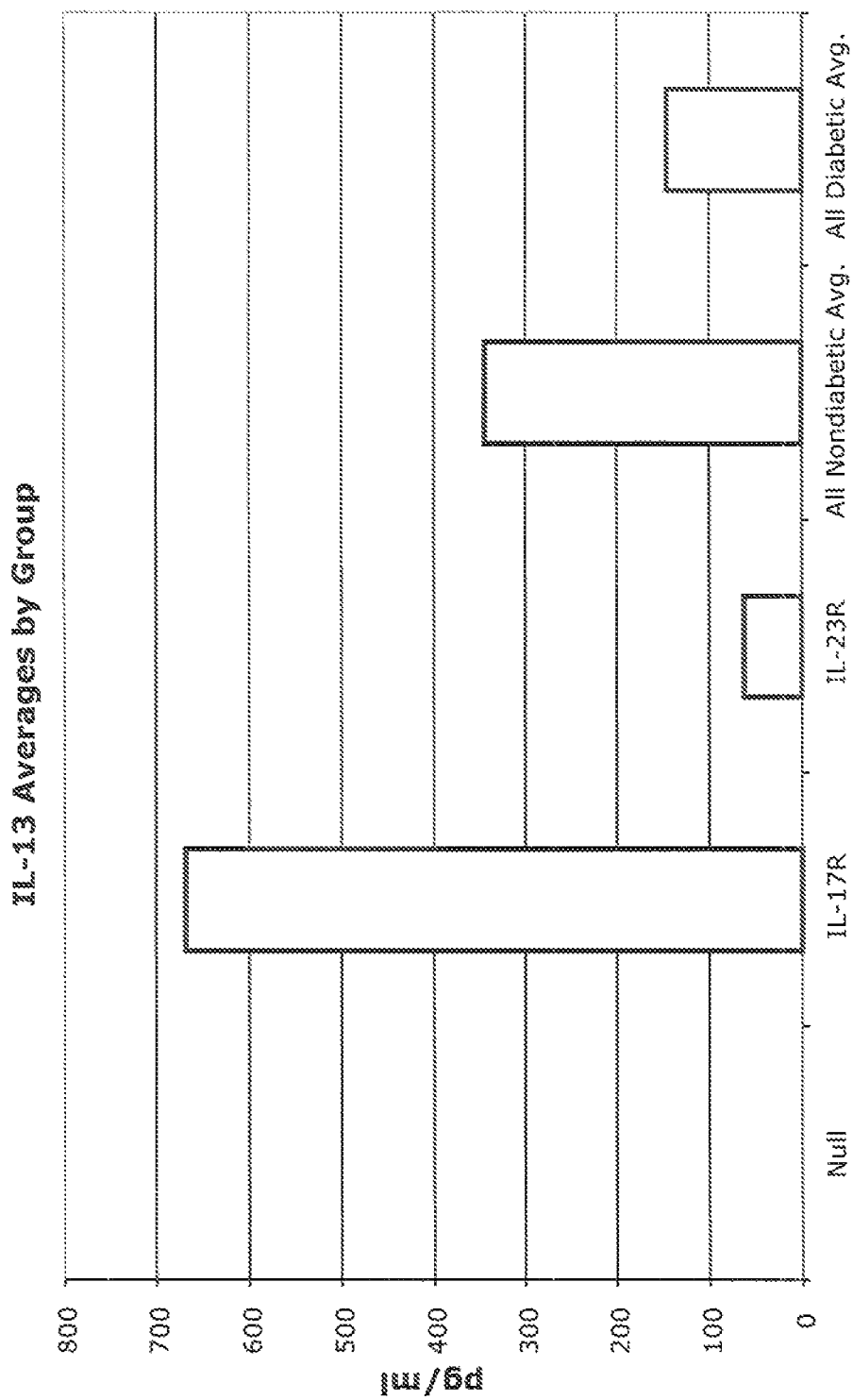
FIG. 13 shows AAV1/IL-17R/9gly/CH3 injection and AAV1/IL-23R/9gly/CH3 injection lead to an increase in IL-13 levels relative to AAV1/null. By comparison, non-diabetic NOD mice in this study had higher IL-13 levels than diabetic NOD mice.
Figure 14:
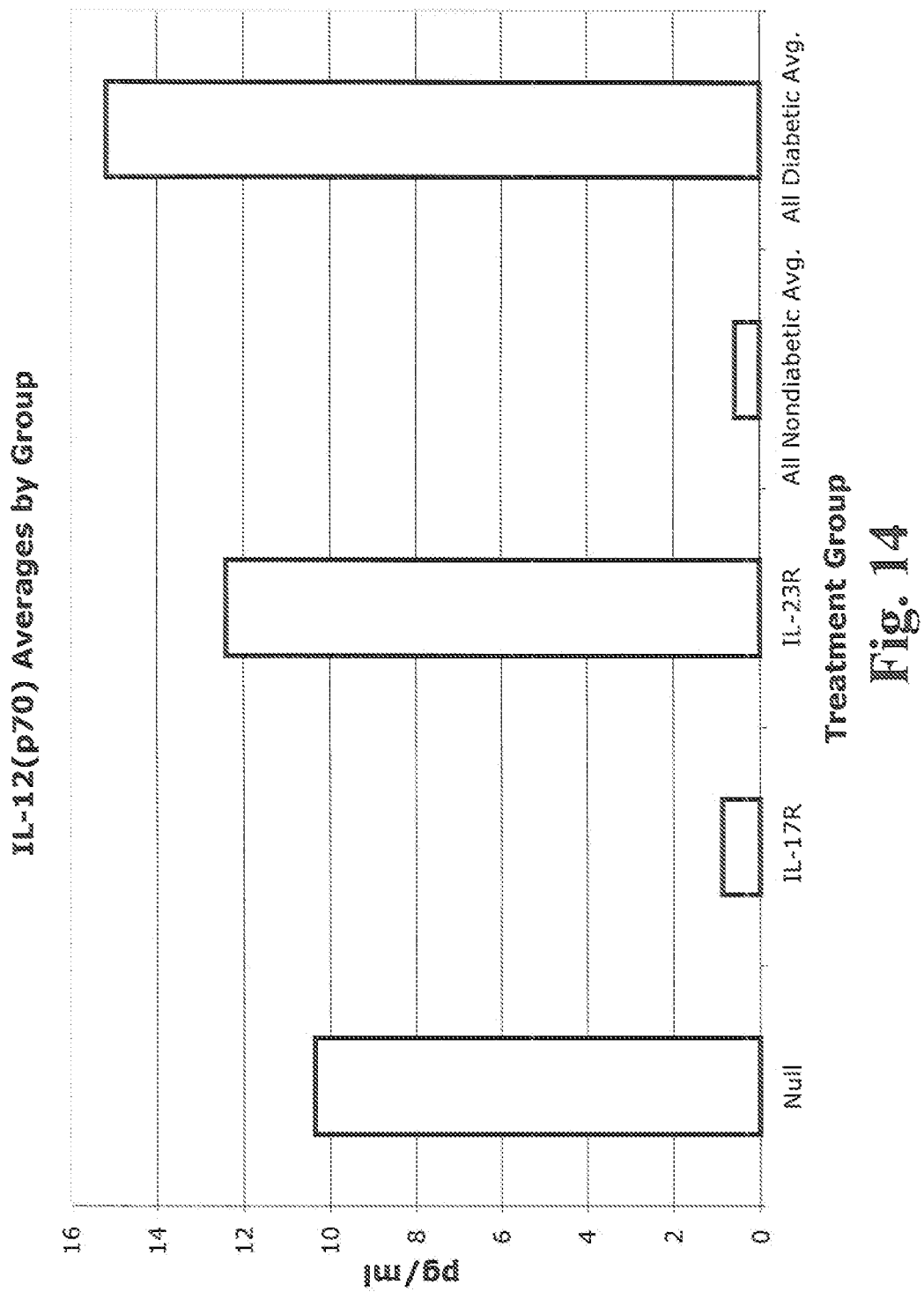
FIG. 14 shows AAV1/IL-17R/9gly/CH3 injection leads to a decrease in IL-12(p70) levels relative to AAV1/null and AAV1/IL-23R/9gly/CH3. By comparison, non-diabetic NOD mice in this study had lower IL-12(p70) levels than the diabetic NOD mice.
Figure 15:
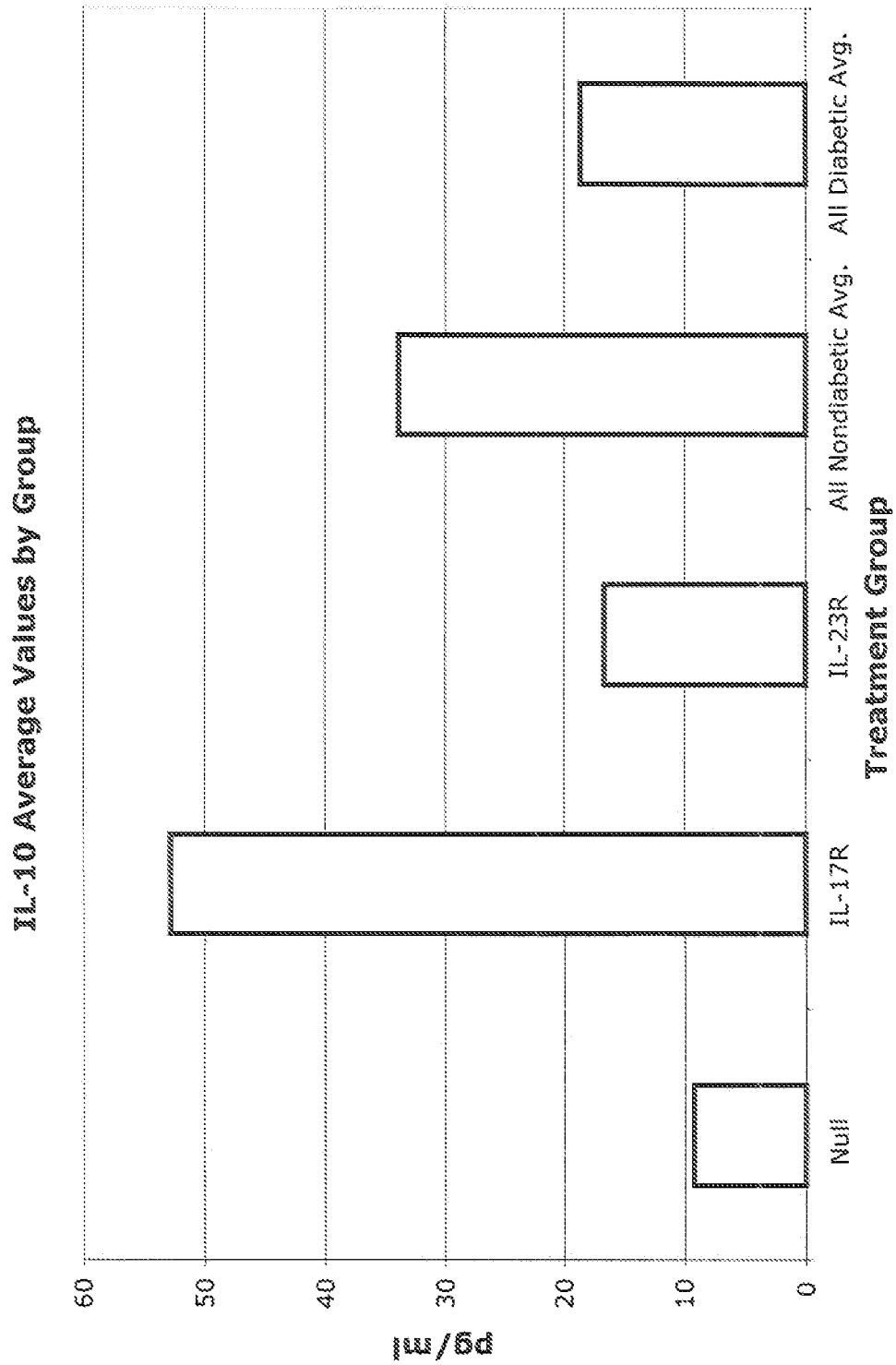
FIG. 15 shows AAV1/IL-17R/9gly/CH3 injection and AAV1/IL-23R/9gly/CH3 injection lead to an increase in IL-10 levels relative to AAV1/null. By comparison, non-diabetic NOD mice in this study had higher IL-10 levels than the diabetic NOD mice.

Results are shown in FIG. 10. Binding is shown relative to the sIL-17r/Fc chimera (R&D Systems, Minneapolis, Minn.). As can be seen, the IL-17r/9gly/CH3 construct bound strongly to IL-17 in the competition ELISA.

Example 3

Description of NOD Mouse Study

The in vivo study consisted of three groups of 20 female non-obese diabetic (NOD) mice. Mice in each group were injected at 10 weeks of age intravenously with $10^{11}$ DNase-resistant AAV particles (DRP). Test particles were AAV1/null, AAV1/IL-17R/9gly/CH3, and AAV1/IL-23R/9gly/CH3.

Figure 16:
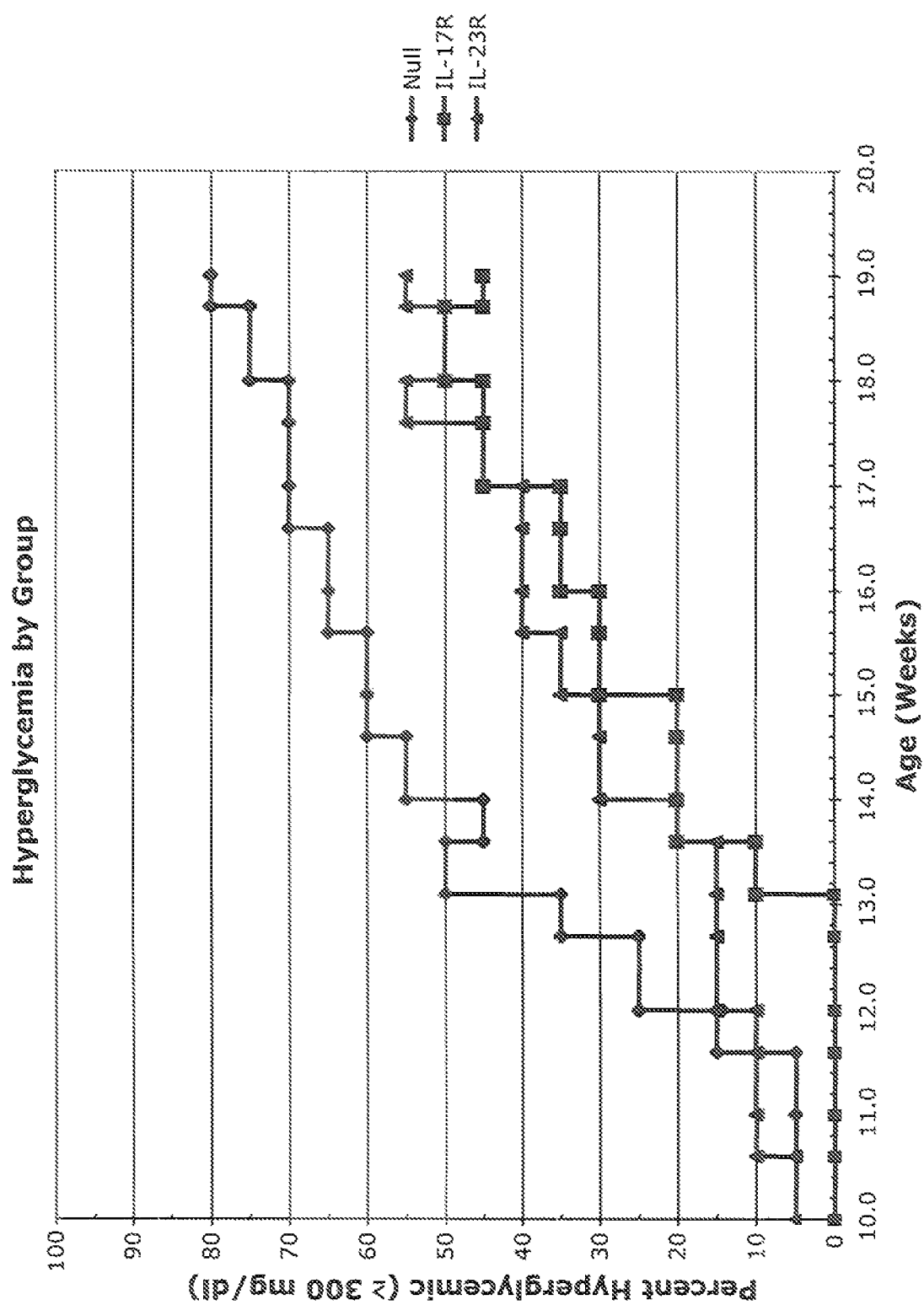
FIG. 16 shows blood glucose levels in three groups of NOD mice treated with one of three AAV vector: AAV1-null, AAV1/IL-17R/9gly/CH3 or AAV1/IL-23R/9gly/CH3.

Blood Glucose Measurements:

Blood from each mouse was taken by tail nick twice weekly beginning two days post-injection for blood glucose measurements. FIG. 16 graphs onset of hypereglycemia (defined as blood glucose ≥300 mg/dl) for each group. Diabetes onset was delayed in the groups receiving AAV expressing soluble cytokine receptors relative to the null group.

Cytokine Quantification:

For cytokine ELISAs, serum was taken from each mouse four weeks and eight weeks post-injection, respectively. FIGS. 11 to 15 show results from a typical assay. In this case, sera from all time points were pooled by treatment group. Cytokine levels were measured using the Millipore Beadlyte Mouse 21-plex Cytokine Detection System. Samples were read on a Luminex 2000 instrument.

Additionally, average cytokine levels were calculated for all non-diabetic mice (blood glucose <300 mg/dL) or diabetic mice, and plotted for comparison purposes.

Thus, compositions comprising IL-23r-immunoglobulin fusions, IL-17r-immunoglobulin fusions, as well as methods for delivering these receptors in order to modulate the effects of IL-23 and IL-17, such as by inhibiting the IL-23 and IL-17 pathways, are described. Although preferred embodiments of the subject invention have been described in some detail, it is understood that obvious variations can be made without departing from the spirit and the scope of the invention as defined herein.

The invention claimed is:

1. An IL-17 receptor fusion protein comprising the amino acid sequence of SEQ ID NO: 8.

* * * * *

SEQUENCE LISTING

<160> NUMBER OF SEQ ID NOS: 17

<210> SEQ ID NO 1
<211> LENGTH: 2601
<212> TYPE: DNA
<213> ORGANISM: Homo sapiens
<220> FEATURE:
<221> NAME/KEY: misc_feature
<223> OTHER INFORMATION: Human IL-17r

<400> SEQUENCE: 1

```
atggggccg cacgcagccc gccgtccgct gtcccggggc ccctgctggg gctgctcctg      60
ctgctcctgg gcgtgctggc cccgggtggc gcctccctgc gactcctgga ccaccgggcg     120
ctggtctgct cccagccggg gctaaactgc acggtcaaga atagtacctg cctggatgac     180
agctggattc accctcgaaa cctgaccccc tcctccccaa aggacctgca gatccagctg     240
cactttgccc acacccaaca aggagacctg ttcccgtgg ctcacatcga atggacactg     300
cagacagacg ccagcatcct gtacctcgag ggtgcagagt tatctgtcct gcagctgaac     360
accaatgaac gtttgtgcgt caggtttgag tttctgtcca aactgaggca tcaccacagg     420
cggtggcgtt ttaccttcag ccactttgtg gttgaccctg accaggaata tgaggtgacc     480
gttcaccacc tgcccaagcc catccctgat ggggacccaa accaccagtc caagaatttc     540
cttgtgcctg actgtgagca cgccaggatg aaggtaacca cgccatgcat gagctcaggc     600
agcctgtggg accccaacat caccgtggag accctggagg cccaccagct gcgtgtgagc     660 ttcacctgt ggaacgaatc tacccattac cagatcctgc tgaccagttt tccgcacatg     720
gagaaccaca gttgctttga gcacatgcac cacatacctg cgcccagacc agaagagttc     780
caccagcgat ccaacgtcac actcactcta cgcaaccta aagggtgctg tcgccaccaa     840
gtgcagatcc agcccttctt cagcagctgc ctcaatgact gcctcagaca ctccgcgact     900
gtttcctgcc cagaaatgcc agacactcca gaaccaattc cggactacat gcccctgtgg     960
gtgtactggt tcatcacggg catctccatc ctgctggtgg gctccgtcat cctgctcatc    1020
gtctgcatga cctggaggct agctgggcct ggaagtgaaa aatacagtga tgacaccaaa    1080
tacaccgatg gcctgcctgc ggctgacctg atcccccac cgctgaagcc caggaaggtc    1140
tggatcatct actcagccga ccaccccctc tacgtggacg tggtcctgaa attcgcccag    1200
ttcctgctca ccgcctgcgg cacggaagtg gccctggacc tgctggaaga gcaggccatc    1260
tcggaggcag gagtcatgac ctgggtggc cgtcagaagc aggagatggt ggagagcaac    1320
tctaagatca tcgtcctgtg ctcccgcggc acgcgcgcca gtggcaggc gctccctggc    1380
```

```
cgggggcgc ctgtgcggct gcgctgcgac cacggaaagc ccgtgggga cctgttcact    1440 gcagccatga acatgatcct cccggacttc aagaggccag cctgcttcgg cacctacgta    1500
gtctgctact tcagcgaggt cagctgtgac ggcgacgtcc ccgacctgtt cggcgcggcg    1560
ccgcggtacc cgctcatgga caggttcgag gaggtgtact ccgcatcca ggacctggag     1620 atgttccagc cgggccgcat gcaccgcgta ggggagctgt cggggacaa ctacctgcgg     1680 agcccgggcg gcaggcagct ccgcgccgcc tggacaggt ccgggactg gcaggtccgc     1740 tgtcccgact ggttcgaatg tgagaacctc tactcagcag atgaccagga tgccccgtcc    1800
ctggacgaag aggtgtttga ggagccactg ctgcctccgg aaccggcat cgtgaagcgg    1860 gcgcccctgg tgcgcgagcc tggctcccag gcctgcctgg ccatagaccc gctggtcggg    1920
gaggaaggag gagcagcagt ggcaaagctg aacctcacc tgcagccccg ggtcagcca    1980 gcgccgcagc ccctccacac cctggtgctc gccgcagagg agggggcct ggtggccgcg    2040 gtggagcctg ggcccctggc tgacggtgcc gcagtccggc tggcactggc ggggaggc    2100 gaggcctgcc cgctgctggg cagcccgggc gctgggcgaa atagcgtcct cttcctcccc    2160 gtggacccccg aggactcgcc ccttggcagc agcacccca tggcgtctcc tgacctcctt     2220
ccagaggacg tgagggagca cctcgaaggc ttgatgctct cgctcttcga gcagagtctg    2280
agctgccagg cccagggggg ctgcagtaga cccgccatgg tcctcacaga cccacacacg    2340
ccctacgagg aggagcagcg gcagtcagtg cagtctgacc agggctacat ctccaggagc    2400
tccccgcagc cccccgaggg actcacggaa atggaggaag aggaggaaga ggagcaggac    2460
ccagggaagc cggccctgcc actctctccc gaggacctgg agagcctgag gagcctccag    2520
cggcagctgc ttttccgcca gctgcagaag aactcgggct gggacacgat ggggtcagag    2580
tcagaggggc ccagtgcatg a                                              2601

<210> SEQ ID NO 2
<211> LENGTH: 866
<212> TYPE: PRT
<213> ORGANISM: Homo sapiens
<220> FEATURE:
<221> NAME/KEY: misc_feature
<223> OTHER INFORMATION: Human IL-17r

<400> SEQUENCE: 2

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
```

```
              130                 135                 140
Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                    165                 170                 175

Ser Lys Asn Phe Leu Val Pro Asp Cys Glu His Ala Arg Met Lys Val
                180                 185                 190

Thr Thr Pro Cys Met Ser Ser Gly Ser Leu Trp Asp Pro Asn Ile Thr
            195                 200                 205

Val Glu Thr Leu Glu Ala His Gln Leu Arg Val Ser Phe Thr Leu Trp
        210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                    245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
            275                 280                 285

Ser Cys Leu Asn Asp Cys Leu Arg His Ser Ala Thr Val Ser Cys Pro
        290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                    325                 330                 335

Ile Leu Leu Ile Val Cys Met Thr Trp Arg Leu Ala Gly Pro Gly Ser
                340                 345                 350

Glu Lys Tyr Ser Asp Asp Thr Lys Tyr Thr Asp Gly Leu Pro Ala Ala
            355                 360                 365

Asp Leu Ile Pro Pro Pro Leu Lys Pro Arg Lys Val Trp Ile Ile Tyr
        370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                    405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
            435                 440                 445

Arg Gly Thr Arg Ala Lys Trp Gln Ala Leu Leu Gly Arg Gly Ala Pro
        450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                    485                 490                 495

Gly Thr Tyr Val Val Cys Tyr Phe Ser Glu Val Ser Cys Asp Gly Asp
                500                 505                 510

Val Pro Asp Leu Phe Gly Ala Ala Pro Arg Tyr Pro Leu Met Asp Arg
            515                 520                 525

Phe Glu Glu Val Tyr Phe Arg Ile Gln Asp Leu Glu Met Phe Gln Pro
        530                 535                 540

Gly Arg Met His Arg Val Gly Glu Leu Ser Gly Asp Asn Tyr Leu Arg
545                 550                 555                 560
```

Ser Pro Gly Gly Arg Gln Leu Arg Ala Ala Leu Asp Arg Phe Arg Asp
            565                 570                 575

Trp Gln Val Arg Cys Pro Asp Trp Phe Glu Cys Glu Asn Leu Tyr Ser
        580                 585                 590

Ala Asp Asp Gln Asp Ala Pro Ser Leu Asp Glu Glu Val Phe Glu Glu
    595                 600                 605

Pro Leu Leu Pro Pro Gly Thr Gly Ile Val Lys Arg Ala Pro Leu Val
610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
            645                 650                 655

Arg Gly Gln Pro Ala Pro Gln Pro Leu His Thr Leu Val Leu Ala Ala
        660                 665                 670

Glu Glu Gly Ala Leu Val Ala Ala Val Glu Pro Gly Pro Leu Ala Asp
    675                 680                 685

Gly Ala Ala Val Arg Leu Ala Leu Ala Gly Glu Gly Glu Ala Cys Pro
690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
            725                 730                 735

Pro Asp Leu Leu Pro Glu Asp Val Arg Glu His Leu Glu Gly Leu Met
        740                 745                 750

Leu Ser Leu Phe Glu Gln Ser Leu Ser Cys Gln Ala Gln Gly Gly Cys
    755                 760                 765

Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
            805                 810                 815

Glu Glu Gln Asp Pro Gly Lys Pro Ala Leu Pro Leu Ser Pro Glu Asp
        820                 825                 830

Leu Glu Ser Leu Arg Ser Leu Gln Arg Gln Leu Leu Phe Arg Gln Leu
    835                 840                 845

Gln Lys Asn Ser Gly Trp Asp Thr Met Gly Ser Glu Ser Glu Gly Pro
850                 855                 860

Ser Ala
865

<210> SEQ ID NO 3
<211> LENGTH: 1890
<212> TYPE: DNA
<213> ORGANISM: Homo sapiens
<220> FEATURE:
<221> NAME/KEY: misc_feature
<223> OTHER INFORMATION: Human IL-23r

<400> SEQUENCE: 3
atgaatcagg tcactattca atgggatgca gtaatagccc tttacatact cttcagctgg     60
tgtcatggag gaattacaaa tataaactgc tctggccaca tctgggtaga accagccaca     120
atttttaaga tgggtatgaa tatctctata tattgccaag cagcaattaa gaactgccaa     180
ccaaggaaac ttcatttttt aaaaatggca tcaagaaaa gatttcaaat cacaaggatt     240

```
aataaaacaa cagctcggct ttggtataaa aactttctgg aaccacatgc ttctatgtac      300
tgcactgctg aatgtcccaa acattttcaa gagacactga tatgtggaaa agacatttct      360
tctggatatc cgccagatat tcctgatgaa gtaacctgtg tcatttatga atattcaggc      420
aacatgactt gcacctggaa tgctgggaag ctcacctaca tagacacaaa atacgtggta      480
catgtgaaga gtttagagac agaagaagag caacagtatc tcacctcaag ctatattaac      540
atctccactg attcattaca aggtggcaag aagtacttgg tttgggtcca agcagcaaac      600
gcactaggca tggaagagtc aaaacaactg caaattcacc tggatgatat agtgatacct      660
tctgcagccg tcatttccag ggctgagact ataaatgcta cagtgcccaa gaccataatt      720
tattgggata gtcaaacaac aattgaaaag gtttcctgtg aaatgagata caaggctaca      780
acaaaccaaa cttggaatgt taagaatttt gacaccaatt ttacatatgt gcaacagtca      840
gaattctact tggagccaaa cattaagtac gtatttcaag tgagatgtca agaaacaggc      900
aaaaggtact ggcagccttg gagttcactg ttttttcata aaacacctga acagttccc       960 caggtcacat caaaagcatt ccaacatgac acatggaatt ctgggctaac agttgcttcc     1020
atctctacag ggcaccttac ttctgacaac agaggagaca ttggactttt attgggaatg     1080
atcgtctttg ctgttatgtt gtcaattctt tctttgattg ggatatttaa cagatcattc     1140
cgaactggga ttaaaagaag gatcttattg ttaataccaa agtggcttta tgaagatatt     1200
cctaatatga aaaacagcaa tgttgtgaaa atgctacagg aaaatagtga acttatgaat     1260
aataattcca gtgagcaggt cctatatgtt gatcccatga ttacagagat aaaagaaatc     1320
ttcatcccag aacacaagcc tacagactac aagaaggaga tacaggaccc ctggagaca     1380 agagactacc cgcaaaactc gctattcgac aatactacag ttgtatatat tcctgatctc     1440
aacactggat ataaacccca aatttcaaat tttctgcctg agggaagcca tctcagcaat     1500
aataatgaaa ttacttcctt aacacttaaa ccaccagttg attccttaga ctcaggaaat     1560
aatcccaggt tacaaaagca tcctaatttt gcttttttctg tttcaagtgt gaattcacta     1620
agcaacacaa tatttcttgg agaattaagc ctcatattaa atcaaggaga atgcagttct     1680
cctgacatac aaaactcagt agaggaggaa accaccatgc ttttggaaaa tgattcaccc     1740
agtgaaacta ttccagaaca gaccctgctt cctgatgaat ttgtctcctg tttggggatc     1800
gtgaatgagg agttgccatc tattaatact tattttccac aaaatatttt ggaaagccac     1860
ttcaatagga tttcactctt ggaaaagtag                                      1890
```

<210> SEQ ID NO 4
<211> LENGTH: 629
<212> TYPE: PRT
<213> ORGANISM: Homo sapiens
<220> FEATURE:
<221> NAME/KEY: misc_feature
<223> OTHER INFORMATION: Human IL-23r

<400> SEQUENCE: 4

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

```
His Phe Tyr Lys Asn Gly Ile Lys Glu Arg Phe Gln Ile Thr Arg Ile
 65                  70                  75                  80

Asn Lys Thr Thr Ala Arg Leu Trp Tyr Lys Asn Phe Leu Glu Pro His
                 85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480
```

```
Asn Thr Gly Tyr Lys Pro Gln Ile Ser Asn Phe Leu Pro Glu Gly Ser
            485                 490                 495

His Leu Ser Asn Asn Asn Glu Ile Thr Ser Leu Thr Leu Lys Pro Pro
        500                 505                 510

Val Asp Ser Leu Asp Ser Gly Asn Asn Pro Arg Leu Gln Lys His Pro
        515                 520                 525

Asn Phe Ala Phe Ser Val Ser Ser Val Asn Ser Leu Ser Asn Thr Ile
        530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
            565                 570                 575

Asn Asp Ser Pro Ser Glu Thr Ile Pro Glu Gln Thr Leu Leu Pro Asp
            580                 585                 590

Glu Phe Val Ser Cys Leu Gly Ile Val Asn Glu Glu Leu Pro Ser Ile
            595                 600                 605

Asn Thr Tyr Phe Pro Gln Asn Ile Leu Glu Ser His Phe Asn Arg Ile
        610                 615                 620

Ser Leu Leu Glu Lys
625

<210> SEQ ID NO 5
<211> LENGTH: 1389
<212> TYPE: DNA
<213> ORGANISM: Artificial Sequence
<220> FEATURE:
<223> OTHER INFORMATION: Synthetic construct sIL23R-9gly-CH3

<400> SEQUENCE: 5
atgaatcatg tcactattca atgggatgca gtaatagccc tttacatact cttcagctgg      60
tgtcatggag gaattacaaa tataaactgc tctggccaca tctgggtaga accagccaca     120
attttaaga tgggtatgaa tatctctata tattgccaag cagcaattaa gaactgccaa     180
ccaaggaaac ttcatttta taaaaatggc atcaagaaa gatttcaaat cacaaggatt     240
aataaaacaa cagctcggct ttggtataaa aactttctgg aaccacatgc ttctatgtac     300
tgcactgctg aatgtcccaa acattttcaa gagacactga tatgtggaaa agacatttct     360
tctggatatc cgccagatat tcctgatgaa gtaacctgtg tcatttatga atattcaggc     420
aacatgactt gcacctggaa tgctgggaag ctcacctaca tagacacaaa atacgtggta     480
catgtgaaga gtttagagac agaagaagag caacagtatc tcacctcaag ctatattaac     540
atctccactg attcattaca aggtggcaag aagtacttgg tttgggtcca agcagcaaac     600
gcactaggca tggaagagtc aaaacaactg caaattcacc tggatgatat agtgatacct     660
tctgcagccg tcatttccag ggctgagact ataaatgcta cagtgcccaa gaccataatt     720
tattgggata gtcaaacaac aattgaaaag gtttcctgtg aaatgagata caaggctaca     780
acaaaccaaa cttggaatgt taagaattt gacaccaatt tacatatgt gcaacagtca     840
gaattctact ggagccaaaa cattaagtac gtatttcaag tgagatgtca agaaacaggc     900
aaaaggtact ggcagccttg gagttcaccg ttttttcata aaaacctga acagttccc     960
caggtcacat caaaagcatt ccaacatgac acatggaatt ctgggctaac agttgcttcc    1020
atctctacag ggcaccttac cggtggaggt ggaggtggag gtggaggtca gccccgagaa    1080
ccacaggtgt acaccctgcc ccatccccgg gatgagctga ccaagaacca ggtcagcctg    1140
acctgcctgg tcaaaggctt ctatcccagc gacatcgccg tggagtggga gagcaatggg    1200
```

```
cagccggaga caactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatag                                                             1389
```

<210> SEQ ID NO 6
<211> LENGTH: 462
<212> TYPE: PRT
<213> ORGANISM: Artificial Sequence
<220> FEATURE:
<223> OTHER INFORMATION: Synthetic construct SIL23R-9gly-CH3

<400> SEQUENCE: 6

```
Met Asn His Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Pro Phe Phe His Lys Thr Pro Glu Thr Val Pro
305                 310                 315                 320
```

Gln Val Thr Ser Lys Ala Phe Gln His Asp Thr Trp Asn Ser Gly Leu
              325                 330                 335

Thr Val Ala Ser Ile Ser Thr Gly His Leu Thr Gly Gly Gly Gly Gly
            340                 345                 350

Gly Gly Gly Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 7
<211> LENGTH: 1302
<212> TYPE: DNA
<213> ORGANISM: Artificial Sequence
<220> FEATURE:
<223> OTHER INFORMATION: Synthetic construct SIL17RA-9gly-CH3

<400> SEQUENCE: 7
atgggggccg cacgcagccc gccgtccgct gtcccggggc ccctgctggg gctgctcctg      60
ctgctcctgg gcgtgctggc cccgggtggc gcctccctgc gactcctgga ccaccgggcg     120
ctggtctgct cccagccggg gctaaactgc acggtcaaga atagtacctg cctggatgac     180
agctggattc accctcgaaa cctgaccccc tcctccccaa aggacctgca gatccagctg     240
cactttgccc acacccaaca aggagacctg ttccccgtgg ctcacatcga atggacactg     300
cagacagacg ccagcatcct gtacctcgag ggtgcagagt tatctgtcct gcagctgaac     360
accaatgaac gtttgtgcgt caggtttgag tttctgtcca aactgaggca tcaccacagg     420
cggtggcgtt ttaccttcag ccactttgtg gttgaccctg accaggaata tgaggtgacc     480
gttcaccacc tgcccaagcc catccctgat ggggacccaa accaccagtc caagaatttc     540
cttgtgcctg actgtgagca cgccaggatg aaggtaacca cgccatgcat gagctcaggc     600
agcctgtggg accccaacat caccgtggag accctggagg ccaccagct cgtgtgagc     660 ttcaccctgt ggaacgaatc tacccattac cagatcctgc tgaccagttt tccgcacatg     720
gagaaccaca gttgctttga gcacatgcac catacctg cgcccagacc agaagagttc     780
caccagcgat ccaacgtcac actcactcta cgcaacctta agggtgctg tcgccaccaa     840 gtgcagatcc agcccttctt cagcagctgc tcaatgact gcctcagaca ctccgcgact     900
gtttcctgcc agaaatgcc agacactcca gaaccaattc cggactacat gaccggtgga     960
ggtggaggtg gaggtggagg tcagccccga gaaccacagg tgtacaccct gcccccatcc    1020
cgggatgagc tgaccaagaa ccaggtcagc ctgacctgcc tggtcaaagg cttctatccc    1080
agcgacatcg ccgtggagtg ggagagcaat gggcagccgg agaacaacta caagaccacg    1140
cctcccgtgc tggactccga cggctccttc ttcctctaca gcaagctcac cgtggacaag    1200
agcaggtggc agcaggggaa cgtcttctca tgctccgtga tgcatgaggc tctgcacaac    1260
cactacacgc agaagagcct ctccctgtct ccgggtaaat ag 1302

<210> SEQ ID NO 8
<211> LENGTH: 433
<212> TYPE: PRT
<213> ORGANISM: Artificial Sequence
<220> FEATURE:
<223> OTHER INFORMATION: Synthetic construct SIL17RA-9gly-CH3

<400> SEQUENCE: 8

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Thr Gly Gly
305                 310                 315                 320

Gly Gly Gly Gly Gly Gly Gln Pro Arg Glu Pro Gln Val Tyr Thr
                325                 330                 335

Leu Pro Pro Ser Arg Asp Glu Leu Thr Lys Asn Gln Val Ser Leu Thr
            340                 345                 350

Cys Leu Val Lys Gly Phe Tyr Pro Ser Asp Ile Ala Val Glu Trp Glu
```

-continued

```
                355                 360                 365
Ser Asn Gly Gln Pro Glu Asn Asn Tyr Lys Thr Thr Pro Pro Val Leu
        370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys

<210> SEQ ID NO 9
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 9

Gly Gly Gly Gly Gly Gly Gly Gly Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 10

Glu Glu Glu Glu Glu Glu Glu Glu Glu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 11

Ser Ser Ser Ser Ser Ser Ser Ser Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 12

Gly Gly Gly Gly Gly Cys Pro Pro Cys
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic linker peptide

<400> SEQUENCE: 13

Gly Gly Gly Gly Ser Gly Gly Gly Gly Ser Gly Gly Gly Gly Ser
```

```
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Synthetic linker peptide

<400> SEQUENCE: 14

Ser Cys Val Pro Leu Met Arg Cys Gly Gly Cys Cys Asn
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic linker peptide

<400> SEQUENCE: 15

Pro Ser Cys Val Pro Leu Met Arg Cys Gly Gly Cys Cys Asn
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic linker peptide

<400> SEQUENCE: 16

Gly Asp Leu Ile Tyr Arg Asn Gln Lys
1               5

<210> SEQ ID NO 17
<211> LENGTH: 23
<212> TYPE: PRT
<213> ORGANISM: Artificial Sequence
<220> FEATURE:
<223> OTHER INFORMATION: Synthetic linker peptide

<400> SEQUENCE: 17

Gly Gly Gly Gly Gly Gly Gly Gly Pro Ser Cys Val Pro Leu Met
1               5                   10                  15

Arg Cys Gly Gly Cys Cys Asn
            20
```